(12) United States Patent
Dolente et al.

(10) Patent No.: US 8,481,528 B2
(45) Date of Patent: Jul. 9, 2013

(54) HETEROBIARYL-CYCLOHEXYL-TETRAAZABENZO[E]AZULENES

(75) Inventors: Cosimo Dolente, Allschwil (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 212 days.

(21) Appl. No.: 13/089,354

(22) Filed: Apr. 19, 2011

(65) Prior Publication Data
US 2011/0263573 A1 Oct. 27, 2011

(30) Foreign Application Priority Data

Apr. 26, 2010 (EP) .................................... 10161043

(51) Int. Cl.
| A61P 9/00 | (2006.01) |
| A61P 15/00 | (2006.01) |
| A61P 25/00 | (2006.01) |
| A61K 31/5517 | (2006.01) |
| C07D 487/04 | (2006.01) |

(52) U.S. Cl.
USPC .......................................... 514/220; 540/563

(58) Field of Classification Search
USPC .......................................... 514/220; 540/563
See application file for complete search history.

(56) References Cited

U.S. PATENT DOCUMENTS

| 7,265,104 | B2 | 9/2007 | Elliott et al. |
| 2002/0103373 | A1 | 8/2002 | Hockstra et al. |
| 2011/0245237 | A1 | 10/2011 | Dolente et al. |
| 2011/0251183 | A1 | 10/2011 | Dolente et al. |
| 2011/0263573 | A1 | 10/2011 | Dolente et al. |
| 2011/0275801 | A1 | 11/2011 | Dolente et al. |

FOREIGN PATENT DOCUMENTS

| EP | 2292621 | 3/2011 |
| KR | 2007/020462 | 2/2007 |
| WO | 96/22292 | 7/1996 |
| WO | 02/083681 | 10/2002 |
| WO | 2004/074291 | 9/2004 |
| WO | 2005/068466 | 7/2005 |
| WO | 2006/021882 | 3/2006 |
| WO | 2006/114706 | 11/2006 |
| WO | 2006/123242 | 11/2006 |
| WO | 2008/084005 | 7/2008 |
| WO | 2010/057795 | 5/2010 |

OTHER PUBLICATIONS

Landgraf et al., Regul. Pept. 59:229-239 ( 1995).
(Opposition in Costa Rican Appl. No. 2011-0220 Sep. 20, 2011).
Van Kerckhoven et al., Eur. J. Pharrnacol, 449:135-141 ( 2002).
Ebner et al., Eur. J. Neurosci. 15:384-388 ( 2002).
Altemus et al., Arch. Gen. Psychiatry 49:9-20 ( 1992).
Regier et al., Br. J. Psychiatry Suppl.:24-28 ( 1998).
Aughton et al., Br. J. Pharmacol.:253 ( 2008).
Robben et al., Am. J. Physiol. Renal. Physiol, 291:F257-270 ( 2006).
(International Search Report PCT/EP2011/058071 May 12, 2011).
Gupta et al., Br. J. Pharmacol. 155:118-126 ( 2008).
Raskind et al., Biol. Psychiatry 22:453-462 ( 1987).
Neumann, J. Neuroendocrinol. 20:858-865 ( 2008).
Bielsky et al., Neurcpsychopharmacology 29:483-493 ( 2004).
Brouard et al., Bjog. 107:614-619 ( 2000).
Michelini et al., Ann. NY Academy Science 897:198-211 ( 1999).
Yirmiya et al., 11:488-494 ( 2006).
Kendler et al., Arch. Gen. Psychiatry 60:789-798 ( 2003).
Thompson et al., Psychoneuroendocrinology 29:35-48 ( 2004).
Gal et al., Progress in Brain Research, Elsevier 139:197-210 XP001205440 ( 2002).
(International Search Report for PCT/EP2011/057368 Jul. 14, 2011).
(International Search Report for PCT/EP2009/064804 Jan. 14, 2010).
(International Search Report PCT/EP2011/056391 Jun. 27, 2011).
(International Search Report for PCT/EP2011/054582 Mar. 25, 2011).
(International Search Report PCT/EP2009/065354 Feb. 8, 2010).
Ebner et al., Eur. J. Neuoscience 15:384-388 ( 2002).
Liebsch et al., Regulatory Peptides 59(2):229-239 ( 1995).
(International Search Report PCT/EP2011/055516 May 23, 2011).

Primary Examiner — Brenda Coleman

(57) ABSTRACT

The present invention relates to heterobiaryl-cyclohexyl-tetraazabenzo[e]azulenes of formula I

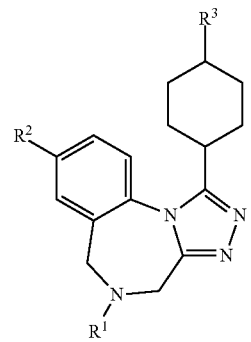

wherein $R^1$, $R^2$ and $R^3$ are as described herein. The compounds according to the invention act as V1a receptor modulators, and in particular as V1a receptor antagonists, their manufacture, pharmaceutical compositions containing them and their use as medicaments. The active compounds of the present invention are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

13 Claims, No Drawings

HETEROBIARYL-CYCLOHEXYL-TETRAAZABENZO[E]AZULENES

PRIORITY TO RELATED APPLICATION(S)

This application claims the benefit of European Patent Application No. 10161043.4, filed Apr. 26, 2010, which is hereby incorporated by reference in its entirety.

BACKGROUND OF THE INVENTION

Vasopressin is a 9 amino acid peptide mainly produced by the paraventricular nucleus of the hypothalamus. In the periphery vasopressin acts as a neurohormone and stimulates vasoconstriction, glycogenolysis and antidiuresis.

Three vasopressin receptors, all belonging to the class I G-protein coupled receptors, are known. The V1a receptor is expressed in the brain, liver, vascular smooth muscle, lung, uterus and testis, the V1b or V3 receptor is expressed in the brain and pituitary gland, the V2 receptor is expressed in the kidney where it regulates water reabsorption and mediates the antidiuretic effects of vasopressin (Robben, et al. (2006). Am J Physiol Renal Physiol. 291, F257-70, "Cell biological aspects of the vasopressin type-2 receptor and aquaporin 2 water channel in nephrogenic diabetes insipidus"). Compounds with activity at the V2 receptor can therefore cause side-effects on blood homeostasis.

The oxytocin receptor is related to the Vasopressin receptor family and mediates the effects of the neurohormone oxytocin in the brain and the periphery. Oxytocin is believed to have central anxiolytic effects (Neumann (2008). J Neuroendocrinol. 20, 858-65, "Brain oxytocin: a key regulator of emotional and social behaviors in both females and males"). Central oxytocin receptor antagonism might therefore lead to anxiogenic effects, which are regarded as undesired side-effects.

In the brain vasopressin acts as a neuromodulator and is elevated in the amygdala during stress (Ebner, et al. (2002). Eur J Neurosci. 15, 384-8, "Forced swimming triggers vasopressin release within the amygdala to modulate stress-coping strategies in rats"). It is known that stressful life events can trigger major depression and anxiety (Kendler, et al. (2003). Arch Gen Psychiatry. 60, 789-96, "Life Event Dimensions of Loss, Humiliation, Entrapment, and Danger in the Prediction of Onsets of Major Depression and Generalized Anxiety") and that both have very high comorbidity, with anxiety often preceding major depression (Regier, et al. (1998). Br J Psychiatry Suppl. 24-8, "Prevalence of anxiety disorders and their comorbidity with mood and addictive disorders"). The V1a receptor is extensively expressed in the brain and particularly in limbic areas like the amygdala, lateral septum and hippocampus which are playing an important role in the regulation of anxiety. Indeed V1a knock-out mice show a reduction in anxious behavior in the plus-maze, open field and light-dark box (Bielsky, et al. (2004). Neuropsychopharmacology. 29, 483-93, "Profound impairment in social recognition and reduction in anxiety-like behavior in vasopressin V1a receptor knockout mice"). The downregulation of the V1a receptor using antisense oligonucleotide injection in the septum also causes a reduction in anxious behavior (Landgraf, et al. (1995). Regul Pept. 59, 229-39, "V1 vasopressin receptor antisense oligodeoxynucleotide into septum reduces vasopressin binding, social discrimination abilities, and anxiety-related behavior in rats"). Vasopressin or the V1a receptor are also implicated in other neuropsychological disorders: genetic studies recently linked sequence polymorphism in the promoter of the human V1a receptor to autistic spectrum disorders (Yirmiya, et al. (2006). 11, 488-94, "Association between the arginine vasopressin 1a receptor (AVPR1a) gene and autism in a family-based study: mediation by socialization skills"), intranasal administration of vasopressin was shown to influence aggression in human males (Thompson; et al. (2004). Psychoneuroendocrinology. 29, 35-48, "The effects of vasopressin on human facial responses related to social communication") and vasopressin levels were found to be elevated in schizophrenic patients (Raskind, et al. (1987). Biol Psychiatry. 22, 453-62, "Antipsychotic drugs and plasma vasopressin in normals and acute schizophrenic patients") and patients with obsessive-compulsive disorder (Altemus, et al. (1992). Arch Gen Psychiatry. 49, 9-20, "Abnormalities in the regulation of vasopressin and corticotropin releasing factor secretion in obsessive-compulsive disorder").

The V1a receptor is also mediating the cardiovascular effects of vasopressin in the brain by centrally regulating blood pressure and heart rate in the solitary tract nucleus (Michelini and Morris (1999). Ann NY Acad. Sci. 897, 198-211, "Endogenous vasopressin modulates the cardiovascular responses to exercise"). In the periphery it induces the contraction of vascular smooth muscles and chronic inhibition of the Via receptor improves hemodynamic parameters in myocardial infarcted rats (Van Kerckhoven, et al. (2002). Eur J Pharmacol. 449, 135-41, "Chronic vasopressin V(1A) but not V(2) receptor antagonism prevents heart failure in chronically infarcted rats"). Hence, V1a antagonists with improved penetration through the blood-brain barrier are expected to be of advantage.

A vasopressin V1a receptor antagonist was shown to be effective in reducing dysmenorrhea in the clinic (Brouard, et al. (2000). Bjog. 107, 614-9, "Effect of SR49059, an orally active V1a vasopressin receptor antagonist, in the prevention of dysmenorrhea"). V1a receptor antagonism has also been implicated in the treatment of female sexual dysfunction (Aughton, et al. (2008). Br J Pharmacol. doi:10.1038/bjp.2008.253, "Pharmacological profiling of neuropeptides on rabbit vaginal wall and vaginal artery smooth muscle in vitro"). In a recent study V1a receptor antagonists were suggested to have a therapeutic role in both erectile dysfunction and premature ejaculation (Gupta, et al. (2008). Br J Pharmacol. 155, 118-26, "Oxytocin-induced contractions within rat and rabbit ejaculatory tissues are mediated by vasopressin V(1A) receptors and not oxytocin receptors").

FIELD OF THE INVENTION

The present invention relates to heterobiaryl-cyclohexyl-tetraazabenzo[e]azulenes, which act as V1a receptor modulators, and in particular as V1a receptor antagonists, their manufacture, pharmaceutical compositions containing them and their use as medicaments.

SUMMARY OF THE INVENTION

The present invention provides compounds of formula I useful for acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

In particular, the present invention relates to compounds of formula I

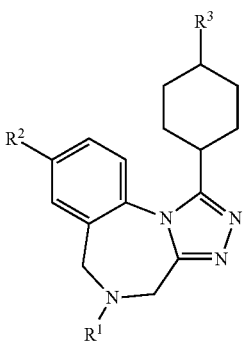

wherein R¹, R² and R³ are as described in herein.

DETAILED DESCRIPTION OF THE INVENTION

The present invention provides compounds which act as V1a receptor modulators, and in particular as V1a receptor antagonists. The invention further provides selective inhibitors of the V1a receptor. It is expected that selectivity affords a low potential to cause unwanted off-target related side effects such as discussed above.

Such V1a antagonists are useful as therapeutics acting peripherally and centrally in the conditions of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior. Particular indications with regard to the present invention are the treatment of anxiety, depressive disorders, obsessive compulsive disorder, autistic spectrum disorders, schizophrenia, and aggressive behavior.

The V1a activity can be detected as described in the experimental section.

The following definitions of the general terms used in the present description apply irrespective of whether the terms in question appear alone or in combination.

As used herein, the terms "$C_{1-6}$-alkyl", alone or in combination with other groups, refers to a hydrocarbon radical that is linear or branched, with single or multiple branching, containing 1 to 6 carbon atoms, for example, methyl (Me), ethyl (Et), propyl, isopropyl (i-propyl), n-butyl, i-butyl (iso-butyl), 2-butyl (sec-butyl), t-butyl (tert-butyl) and the like. Particular alkyl groups are groups with 1 to 4 carbon atoms. More particular are methyl, ethyl and tert-butyl.

The term "$C_{1-6}$-alkoxy", alone or in combination with other groups, denotes a group —O—R' wherein R' is $C_{1-6}$-alkyl as defined above, for example methoxy, ethoxy, propoxy, tert-butoxy and the like. Particular alkoxy groups are groups with 1 to 4 carbon atoms. Particular is methoxy.

The term "aryl" refers to an aromatic carbocyclic group containing 6 to 14, particularly 6 to 10, carbon atoms and having at least one aromatic ring or multiple condensed rings in which at least one ring is aromatic. Examples include phenyl (Ph), benzyl, naphthyl, biphenyl, anthryl, azalenyl or indanyl. Particular is phenyl.

The term "heteroaryl", alone or in combination with other groups, refers to a cyclic aromatic group having a single 5 to 6 membered ring and containing 1, 2 or 3 heteroatoms, in which group at least one heterocyclic ring is aromatic. The term "6-membered heteroaryl" refers to a monocyclic aromatic group having a single 6 membered ring, and containing 1, 2 or 3 heteroatoms independently selected from O, S and N. Particular single 6 membered rings have 1 or 2 N. Examples include pyridinyl, pyrimidinyl, pyrazinyl, pyridazinyl, thiazinyl, oxazinyl and the like. Particular single 6 membered ring is pyridinyl. Specific "6-membered heteroaryl" are attached via a carbon atom to the cyclohexyl-moiety. Particular is pyridin-3-yl. The term "5-membered heteroaryl" refers to a monocyclic aromatic group having a single 5 membered ring, and containing 1, 2 or 3 heteroatoms independently selected from O, S and N. Particular single 5 membered rings have 2 N or 1 O and 1 N. Examples include thiazolyl, isoxazolyl, isothiazolyl, oxadiazolyl, thiadiazolyl and the like. Particular is isoxazolyl. Specific "5-membered heteroaryl" are attached via a carbon atom to the cyclohexyl moiety. Particular is isoxazol-3-yl.

The term "heterobiaryl", alone or in combination with other groups, refers to a cyclic group having a first 4 to 8 membered aromatic ring, preferably 5 to 6 membered aromatic ring, condensed to a second 4 to 8 membered aromatic ring, preferably 5 to 6 membered aromatic ring, and each ring individually comprising 1, 2 or 3 heteroatoms independently selected from O, S and N. Particular are heterobiaryl wherein one ring is phenyl or pyridinyl. More particular is heterobiaryl wherein one ring is phenyl. Examples of heterobiaryl include benzofuryl, isobenzofuryl, indolyl, isoindolyl, benzothiophenyl, benzoimidazolyl, purinyl, indazolyl, benzoxazolyl, benzoisoxazolyl, benzothiazolyl, benzotriazolyl, 1,3-dihydro-2-indoxyl, benzoisothiazolyl, chinolinyl, chinoxalinyl, chinazolinyl, cinnolinyl, 4,5,6,7-tetrahydro-benzoisoxazolyl, isothiazolo[4,5-b]pyridinyl, and the like. Particular are benzoisoxazolyl, 4,5,6,7-tetrahydro-benzoisoxazolyl, benzoisothiazolyl, isothiazolo[5,4-b]pylidinyl, isothiazolo[4,5-b]pyridinyl and isothiazolo[4,5-c]pyridinyl. Specific "heterobiaryl" are attached via a carbon atom to the cyclohexyl moiety. Particular are benzo[d]isoxazol-3-yl, isoxazolo[4,5-b]pyridin-3-yl, isoxazolo[5,4-b]pyridin-3-yl, benzo[d]isothiazol-3-yl, isothiazolo[4,5-b]pyridin-3-yl, 4-isothiazolo[5,4-c]pyridin-3-yl. More particular are benzo[d]isoxazol-3-yl, isoxazolo[4,5-b]pyridin-3-yl, isothiazolo[4,5-h]pyridin-3-yl, 4-isothiazolo[5,4-c]pyridin-3-yl.

The term "cycloalkyl" refers to a 3 to 8 membered carbon ring, for example cyclopropyl, cyclobutyl, cyclopentyl, cyclohexyl, cycloheptyl or cyclooctyl. Particular are cycloalkyl groups having a 3, 4, 5 or 6 membered carbon ring. Particular is cyclobutyl.

The term "cyano" denotes the group —CN.

The term "hydroxy" denotes the group —OH.

The term "Boc" denotes a group —C(O)O-tert-butyl (—C(O)OC(CH$_3$)$_3$).

The term "S(O)$_2$—$C_{1-6}$-alkyl" refers to an "$C_{1-6}$-alkyl" as defined herein linked via an —S(O)$_2$—.

The term "C(O)—$C_{1-6}$-alkyl" refers to an "$C_{1-6}$-alkyl" as defined herein linked via an —C(=O)—.

The term "C(O)O—$C_{1-6}$-alkyl" refers to an "$C_{1-6}$-alkyl" as defined herein linked via an —C(=O)O—.

The term "halogen", alone or in combination with other groups, denotes chloro (Cl), iodo (I), fluoro (F) and bromo (Br). Specific halogens are F and Cl, particular is Cl.

The term "halogen-$C_{1-6}$-alkyl" refers to a $C_{1-6}$-alkyl group substituted by one or multiple halogen, particular is fluoro-$C_{1-6}$alkyl, for example the following groups: CF$_3$, CHF$_2$, CH$_2$F, CH$_2$CF$_3$, CH$_2$CH$_2$CF$_3$, CF$_2$CHF$_2$, and the like.

The term "hydroxy-$C_{1-6}$-alkyl" refers to a $C_{1-6}$-alkyl group substituted by one or multiple hydroxy, for example the following groups: hydroxymethyl-, 2-hydroxyethyl-, 2-hydroxy-1-methyl-ethyl- or 2-hydroxypropyl- and the like.

The term "cyano-$C_{1-6}$-alkyl" refers to a $C_{1-6}$-alkyl group substituted by one or multiple cyano, for example the following groups: cyanomethyl-, 2-cyanoethyl-, 2-cyano-1-methylethyl- or 2-cyanopropyl- and the like.

The term "halogen-$C_{1-6}$-alkoxy" refers to a $C_{1-6}$-alkoxy group substituted by one or multiple halogen, particular fluoro, i.e. "fluoro-$C_{1-6}$alkoxy", for example the following groups: F—$CH_2$—O—.

The term "heterocyclyl" refers to a 3 to 7-membered heterocyclic ring containing at least one heteroatom, such as N, O or S, the number of N atoms being 0, 1, 2 or 3 and the number of O and S atoms each being 0, 1 or 2. Examples of heterocyclyl groups include pyrrolidinyl, tetrahydrofuryl, tetrahydrothienyl, tetrahydropyridinyl, tetrahydropyryl, azetidinyl, thiazolidinyl, oxazolidinyl, piperidinyl, morpholinyl, thiomorpholinyl, piperazinyl, azepanyl, diazepanyl, oxazepanyl and the like.

The term "optionally substituted" refers to an $C_a$-alkyl or $C_b$-alkyl group, which can be unsubstituted or substituted by 1 to 4 substituents individually selected from the group consisting of OH, halogen, cyano, halogen-$C_{1-6}$-alkoxy and $C_{1-6}$-alkoxy; or a cycloalkyl group which can be unsubstituted or substituted by 1 to 4 substituents individually selected from the group consisting of OH, halogen, cyano, $C_{1-6}$-alkyl, halogen-$C_{1-6}$-alkyl, halogen-$C_{1-6}$-alkoxy and $C_{1-6}$-alkoxy.

The term "pharmaceutically acceptable salts" refers to salts that are suitable for use in contact with the tissues of humans and animals without undue toxicity, irritation, allergic response, and the like. Examples of suitable salts with inorganic and organic acids are, but are not limited to, hydrochloric acid, nitric acid, sulphuric acid, phosphoric acid, sulphuric acid, citric acid, formic acid, fumaric acid, maleic acid, lactic acid, malic acid, acetic acid, succinic acid, tartaric acid, methane-sulfonic acid, p-toluenesulphonic acid, trifluoroacetic acid and the like. Specific is hydrochloric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

"Therapeutically effective amount" means an amount that is effective to prevent, alleviate or ameliorate symptoms of disease or prolong the survival of the subject being treated.

The following table lists abbreviations used within the present document.

TABLE 1

| abbreviations | |
|---|---|
| $(BOC)_2O$ | di-tert-butyl pyrocarbonate |
| $(COCl)_2$ | oxalyl (di)chloride |
| AcOH | acetic acid |
| $CH_2Cl_2$ | dichloromethane |
| $((CH_3)_3CCO)_2O$ | trimethylacetic anhydride |
| CuCl | copper(I) chloride |
| DMF | dimethylformamide |
| DMAP | 4-(dimethylamino)-pyridine |
| DMSO | dimethylsulfoxide |
| (dppf)/$PdCl_2$ | [1,1'-Bis(diphenylphosphino)ferrocene]dichloropalladium(II). |
| EDTA | ethylendiamin tetraacetate |
| $EtN_3$ | triethylamine |
| EtOAc | ethyl acetate |
| EtOH | ethanol |
| HATU | 2-(7-aza-1H-benzotriazole-1-yl)-1,1,3,3-tetramethyluronium hexafluorophosphate |
| HEPES | 2-(4-(2-hydroxyethyl)-1-piperazinyl)-ethanesulfonic acid |
| HF-pyridine | pyridine hydrofluoride |
| $H_2O$ | water |
| $H_2SO_4$ | sulphuric acid |
| HPLC | high performance liquid crystallography |
| $KHF_2$ | potassium bifluoride |
| $K_3PO_4$ | potassium phosphate |
| Lawesson's reagent | 2,4-bis-(4-methoxyphenyl)-1,3,2,4-dithiadiphosphetane-2,4-disulfide |
| MeOH | methanol |
| MS | mass spectroscopy |
| $Na_2CO_3$ | sodium carbonate |
| $NaNO_2$ | sodium nitrite |
| NaOEt | sodium ethoxide |
| NaOH | sodium hydroxide |
| n-BuOH | n-butanol |
| NMR | nuclear magnetic resonance |
| $PdCl_2$ | palladium dichloride |
| $Pd(OAc)_2$ | palladium acetate |
| $Pd(PPh)_3$ | tetrakis(triphenylphosphine)palladium(0) |
| $POCl_3$ | phosphorus oxychloride |

TABLE 1-continued abbreviations

| | |
|---|---|
| PtO₂ | platinum oxide |
| (PPh)₃ | triphenylphosphine |
| RNA | ribonucleic acid |
| RT | room temperature |
| RT-PCR | reverse transcription-polymerase chain reaction |
| SOCl₂ | thionyl chloride |
| t-BuOK | potassium-tert-butoxide |
| THF | tetrahydrofunran |
| Tris | Tris(hydroxymethyl)-aminomethane |
| ZnBr₂ | zinc bromide |

The invention also provides pharmaceutical compositions, methods of using, and methods of preparing the aforementioned compounds.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective spirit and scope of the present invention. All such modifications are intended to be within the scope of the claims appended hereto. All separate embodiments can be combined.

The compounds of formula I can contain asymmetric carbon atoms. Accordingly, the present invention includes all stereoisomeric forms of the compounds of formula I, including each of the individual stereoisomer and mixtures thereof, i.e. their individual optical isomers and mixtures thereof. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separation's can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

This applies in particular to the aryl-head group (HG) of the compounds of formula I, namely

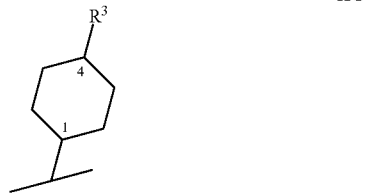

wherein at least the carbon atoms 1 and 4 are asymmetric carbon atoms and $R^3$ could further comprise asymmetric carbon atoms. It is to be understood that present invention includes all individual stereoisomers of head groups and mixtures thereof.

In particular, these head groups HG are

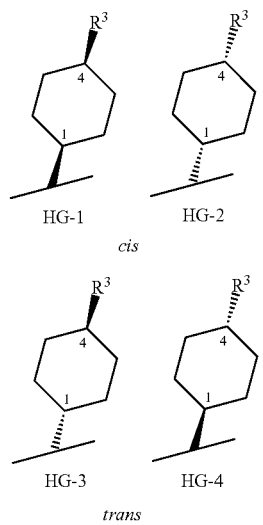

It is further understood that all embodiments of the invention as described herein can be combined with each other.

In detail, the present invention relates to compounds of formula I

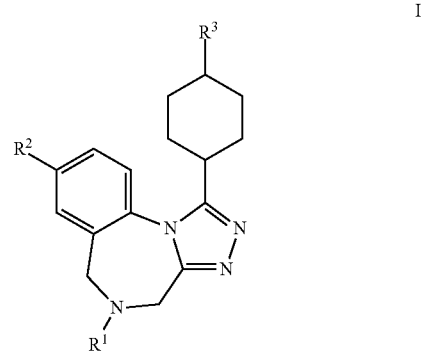

wherein
R¹ is selected from the group consisting of
i) H,
ii) unsubstituted or substituted by 1 to 5 substituents individually selected from the group consisting of OH, halogen, cyano and $C_{1-6}$-alkoxy,
iii) —$S(O)_2$—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
iv) —C(O)—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
v) —C(O)O—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy;
vi) cycloalkyl, unsubstituted or substituted by 1 to 5 substituents individually selected from the group consisting of OH, halogen, cyano, $C_{1-6}$-alkyl and $C_{1-6}$-alkoxy,
vii) $S(O)_2$—$(CH_2)_q$—$NR^iR^{ii}$, wherein
q is 0 or 1,
$R^i$ and $R^{ii}$ is each individually selected from the group consisting of H and $C_{1-6}$-alkyl, or
$R^i$ and $R^{ii}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy,
viii) —$(CH_2)_r$—$NR^{iii}R^{iv}$, wherein
r is 1, 2 or 3,
$R^{iii}$ and $R^{iv}$ is each individually selected from the group consisting of H and $C_{1-6}$-alkyl, or
$R^{iii}$ and $R^{iv}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy, and
ix) —$C(O)(CH_2)_s$—$NR^vR^{vi}$, wherein
s is 1, 2 or 3,
$R^v$ and $R^{vi}$ is each individually selected from the group consisting of H and $C_{1-6}$-alkyl, or
$R^v$ and $R^{vi}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy;
R² is halogen;
R³ is heterobiaryl, unsubstituted or substituted by 1-5 substituents individually selected from the group consisting of OH, halogen, cyano, $C_{1-6}$-alkoxy, halogen-$C_{1-6}$-alkyl, halogen-$C_{1-6}$-alkoxy and hydroxy-$C_{1-6}$-alkyl;
or a pharmaceutically acceptable salt thereof.

A certain embodiment of the invention relates to a compound of formula Ia,

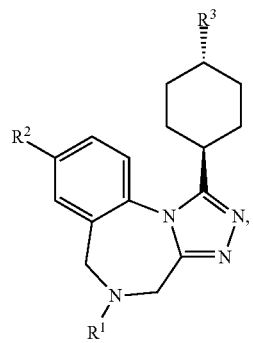

wherein
R¹ is selected from the group consisting of
i) H,
ii) —$C_{1-6}$-alkyl, unsubstituted or substituted by 1 to 5 substituents individually selected from the group consisting of OH, halogen, cyano and $C_{1-6}$-alkoxy,
iii) —$S(O)_2$—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
iv) —C(O)—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
v) —C(O)O—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy;
vi) cycloalkyl, unsubstituted or substituted by 1 to 5 substituents individually selected from the group consisting of OH, halogen, cyano, $C_{1-6}$-alkyl and $C_{1-6}$-alkoxy,
vii) $S(O)_2$—$(CH_2)_q$—$NR^iR^{ii}$, wherein
q is 0 or 1,
$R^i$ and $R^{ii}$ is each individually selected from the group consisting of 1-1 and $C_{1-6}$-alkyl, or
$R^i$ and $R^{ii}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy,
viii) —$(CH_2)_r$—$NR^{iii}R^{iv}$, wherein
r is 1, 2 or 3,
$R^{iii}$ and $R^{iv}$ is each individually selected from the group consisting of H and $C_{1-6}$-alkyl, or
$R^{iii}$ and $R^{iv}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy, and
ix) —$C(O)(CH_2)_s$—$NR^vR^{vi}$, wherein
s is 1, 2 or 3,
$R^v$ and $R^{vi}$ is each individually selected from the group consisting of H and $C_{1-6}$-alkyl, or
$R^v$ and $R^{vi}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy;

$R^2$ is halogen;

$R^3$ is heterobiaryl, unsubstituted or substituted by 1-5 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy and hydroxy-$C_{1-6}$-alkyl;

or a pharmaceutically acceptable salt thereof.

A certain embodiment of the invention relates to a compound of formula I, wherein $R^1$ is selected from the group consisting of
i) H,
ii) —$C_{1-6}$-alkyl,
iii) —$S(O)_2$—$C_{1-6}$-alkyl,
iv) —$C(O)O$—$C_{1-6}$-alkyl,
v) cycloalkyl,
vi) wherein
  r is 1, 2 or 3,
  $R^{iii}$ and $R^{iv}$ is each individually selected from the group consisting of H and $C_{1-6}$-alkyl, and
vii) —$C(O)(CH_2)_s$—$NR^v R^{vi}$, wherein
  s is 1, 2 or 3,
  $R^v$ and $R^{vi}$ is each individually selected from the group consisting of H and $C_{1-6}$-alkyl.

A certain embodiment of the invention relates to a compound of formula I, wherein $R^1$ is selected from the group consisting of H, methyl, cyclobutyl, methyl-2-ethylamine, 1-oxo-ethyl, 1-oxo-2-(dimethylamino)-ethyl and methyl-sulfonyl.

A certain embodiment of the invention relates to a compound of formula I, wherein $R^1$ is selected from the group consisting of —$C_{1-6}$-alkyl, cycloalkyl, —$(CH_2)_2$—$N(C_{1-6}$-alkyl)$_2$ and —$C(O)(CH_2)$—$N(C_{1-6}$-alkyl)$_2$.

A certain embodiment of the invention relates to a compound of formula I, wherein $R^1$ is selected from the group consisting of methyl, cyclobutyl, methyl-2-ethylamine and 1-oxo-2-(dimethylamino)-ethyl.

A certain embodiment of the invention relates to a compound of formula I, wherein $R^1$ is H.

A certain embodiment of the invention relates to a compound of formula I, wherein $R^1$ is A certain embodiment of the invention relates to a compound of formula I, wherein $R^1$ is methyl.

A certain embodiment of the invention relates to a compound of formula I, wherein $R^1$ is —$C(O)O$—$C_{1-6}$-alkyl.

A certain embodiment of the invention relates to a compound of formula I, wherein $R^1$ is Boc.

A certain embodiment of the invention relates to a compound of formula I, wherein $R^1$ is cycloalkyl.

A certain embodiment of the invention relates to a compound of formula I, wherein $R^1$ is cyclobutyl.

A certain embodiment of the invention relates to a compound of formula I, wherein $R^1$ is —$(CH_2)_r$—$NR^{iii}R^{iv}$, wherein r is 1, 2 or 3 and $R^{iii}$ and $R^{iv}$ is each individually selected from the group consisting of H and $C_{1-6}$-alkyl.

A certain embodiment of the invention relates to a compound of formula I, wherein $R^1$ is —$(CH_2)_2$—$N(C_{1-6}$-alkyl)$_2$.

A certain embodiment of the invention relates to a compound of formula I, wherein $R^1$ is methyl-2-ethylamine.

A certain embodiment of the invention relates to a compound of formula I, wherein $R^1$ is —$C(O)$—$C_{1-6}$-alkyl.

A certain embodiment of the invention relates to a compound of formula I, wherein $R^1$ is 1-oxo-ethyl.

A certain embodiment of the invention relates to a compound of formula I, wherein $R^1$ is —$C(O)(CH_2)_s$—$NR^v R^{vi}$, wherein s is 1, 2 or 3 and $R^v$ and $R^{vi}$ is each individually selected from the group consisting of H and $C_{1-6}$-alkyl.

A certain embodiment of the invention relates to a compound of formula I, wherein $R^1$ is —$C(O)(CH_2)$—$N(C_{1-6}$-alkyl)$_2$.

A certain embodiment of the invention relates to a compound of formula I, wherein $R^1$ is 1-oxo-2-(dimethylamino)-ethyl.

A certain embodiment of the invention relates to a compound of formula I, wherein $R^1$ is —$S(O)_2$—$C_{1-6}$-alkyl.

A certain embodiment of the invention relates to a compound of formula I, wherein $R^1$ is methyl-sulfonyl.

A certain embodiment of the invention relates to a compound of formula I, wherein $R^2$ is chloro.

A certain embodiment of the invention relates to a compound of formula I, wherein $R^3$ is heterobiaryl, unsubstituted or substituted by 1-2 halogen.

A certain embodiment of the invention relates to a compound of formula I, wherein $R^3$ is benzo[d]isoxazolyl, isoxazolo[4,5-b]pyridinyl, isoxazolo[5,4-b]pyridinyl, benzo[d]isothiazolyl, isothiazolo[4,5-b]pyridinyl or 4-isothiazolo[5,4-c]pyridinyl, each unsubstituted or substituted by 1-2 halogen.

A certain embodiment of the invention relates to a compound of formula I, wherein $R^3$ is benzo[d]isoxazol-3-yl, 6-fluoro-benzo[d]isoxazol-3-yl, 5-fluoro-benzo[d]isoxazol-3-yl, isoxazolo[4,5-b]pyridin-3-yl, isoxazolo[5,4-b]pyridin-3-yl, benzo[d]isothiazol-3-yl, isothiazolo[4,5-b]pyridin-3-yl or 4-isothiazolo[5,4-c]pyridin-3-yl.

A certain embodiment of the invention relates to a compound of formula I, wherein $R^3$ is benzo[d]isoxazolyl, 6-fluoro-benzo[d]isoxazolyl, 5-fluoro-benzo[d]isoxazolyl, isoxazolo[4,5-b]pyridinyl, isoxazolo[5,4-b]pyridinyl, benzo[d]isothiazolyl, isothiazolo[4,5-b]pyridinyl, 4-isothiazolo[5,4-c]pyridinyl.

A certain embodiment of the invention relates to a compound of formula I, wherein $R^3$ is benzo[d]isoxazol-3-yl, 6-fluoro-benzo[d]isoxazol-3-yl, 5-fluoro-benzo[d]isoxazol-3-yl, isoxazolo[4,5-b]pyridin-3-yl, isoxazolo[5,4-b]pyridin-3-yl, benzo[d]isothiazol-3-yl, isothiazolo[4,5-b]pyridin-3-yl, 4-isothiazolo[5,4-c]pyridin-3-yl.

A certain embodiment of the invention relates to a compound of formula I, wherein $R^3$ is benzo[d]isoxazol-3-yl.

A certain embodiment of the invention relates to a compound of formula I, wherein $R^3$ is 6-fluoro-benzo[d]isoxazol-3-yl.

A certain embodiment of the invention relates to a compound of formula I, wherein $R^3$ is 5-fluoro-benzo[d]isoxazol-3-yl.

A certain embodiment of the invention relates to a compound of formula I, wherein $R^3$ is isoxazolo[4,5-b]pyridin-3-yl.

A certain embodiment of the invention relates to a compound of formula I, wherein $R^3$ is isoxazolo[5,4-b]pyridin-3-yl.

A certain embodiment of the invention relates to a compound of formula I, wherein $R^3$ is benzo[d]isothiazol-3-yl.

A certain embodiment of the invention relates to a compound of formula I, wherein $R^3$ is isothiazolo[4,5-b]pyridin-3-yl.

A certain embodiment of the invention relates to a compound of formula I, wherein $R^3$ is 4-isothiazolo[5,4-c]pyridin-3-yl.

Examples for the compound according to the invention are shown in the experimental part and the table below.

TABLE 2 structures of selected examples

| Ex | Structure |
|---|---|
| 1 | (benzisoxazole-cyclohexyl-triazolo-benzodiazepine with Cl and N-Boc) |
| 2 | (benzisoxazole isomer-cyclohexyl-triazolo-benzodiazepine with Cl and N-Boc) |
| 3 | (benzisoxazole-cyclohexyl-triazolo-benzodiazepine with Cl, NH·ClH) |
| 4 | (benzisoxazole-cyclohexyl-triazolo-benzodiazepine with Cl, N-Me) |
| 5 | (benzisoxazole isomer-cyclohexyl-triazolo-benzodiazepine with Cl, NH·ClH) |

TABLE 2-continued structures of selected examples

| Ex | Structure |
|---|---|
| 6 | (benzisoxazole-cyclohexyl-triazolo-benzodiazepine with Cl, N-Me) |
| 7 | (F-benzisoxazole-cyclohexyl-triazolo-benzodiazepine with Cl, N-Boc) |
| 8 | (F-benzisoxazole-cyclohexyl-triazolo-benzodiazepine with Cl, NH·ClH) |
| 9 | (F-benzisoxazole-cyclohexyl-triazolo-benzodiazepine with Cl, N-Me) |
| 10 | (F-benzisoxazole-cyclohexyl-triazolo-benzodiazepine with Cl, N-Boc) |

TABLE 2-continued structures of selected examples

| Ex | Structure |
|---|---|
| 11 | (6-fluoro-1,2-benzisoxazol-3-yl)cyclohexyl-triazolo-chloro-benzodiazepine, ClH |
| 12 | (6-fluoro-1,2-benzisoxazol-3-yl)cyclohexyl-triazolo-chloro-N-methyl-benzodiazepine |
| 13 | (isoxazolo[4,5-b]pyridin-3-yl)cyclohexyl-triazolo-chloro-benzodiazepine N-Boc |
| 14 | (isoxazolo[4,5-b]pyridin-3-yl)cyclohexyl-triazolo-chloro-benzodiazepine, ClH |
| 15 | (isoxazolo[4,5-b]pyridin-3-yl)cyclohexyl-triazolo-chloro-N-methyl-benzodiazepine |
| 16 | (isoxazolo[5,4-b]pyridin-3-yl)cyclohexyl-triazolo-chloro-benzodiazepine N-Boc |
| 17 | (isoxazolo[5,4-b]pyridin-3-yl)cyclohexyl-triazolo-chloro-benzodiazepine, ClH |
| 18 | (isoxazolo[5,4-b]pyridin-3-yl)cyclohexyl-triazolo-chloro-N-methyl-benzodiazepine |
| 19 | (1,2-benzisothiazol-3-yl)cyclohexyl-triazolo-chloro-benzodiazepine N-Boc |
| 20 | (1,2-benzisothiazol-3-yl)cyclohexyl-triazolo-chloro-benzodiazepine, ClH |

TABLE 2-continued
structures of selected examples
| Ex | Structure |
|----|-----------|
| 21 | 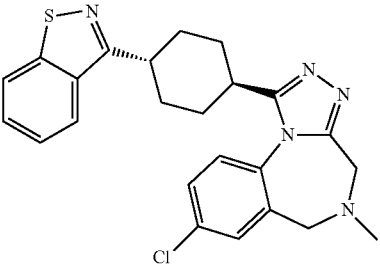 [SMILES: CN1Cc2cc(Cl)ccc2-n2c(nnc2[C@H]2CC[C@H](c3nsc4ccccc43)CC2)C1] |
| 22 | 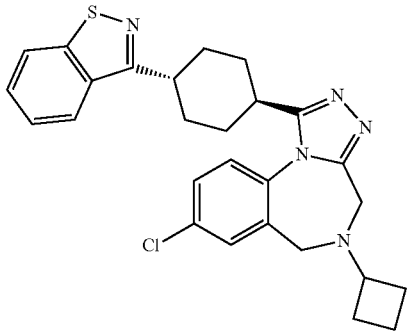 [SMILES: Clc1ccc2c(c1)CN(C1CCC1)Cc1nnc([C@H]3CC[C@H](c4nsc5ccccc54)CC3)n1-2] |
| 23 | 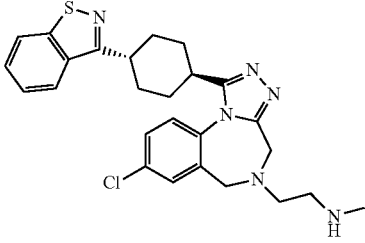 [SMILES: CNCCN1Cc2cc(Cl)ccc2-n2c(nnc2[C@H]2CC[C@H](c3nsc4ccccc43)CC2)C1] |
| 24 | 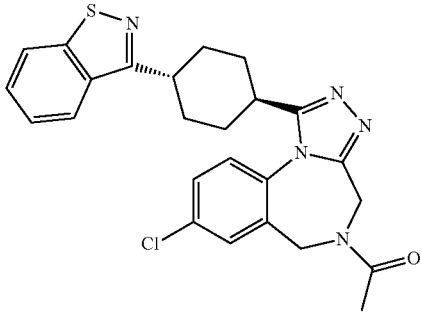 [SMILES: CC(=O)N1Cc2cc(Cl)ccc2-n2c(nnc2[C@H]2CC[C@H](c3nsc4ccccc43)CC2)C1] |
| 25 | 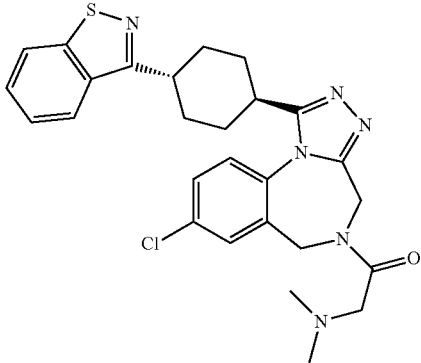 [SMILES: CN(C)CC(=O)N1Cc2cc(Cl)ccc2-n2c(nnc2[C@H]2CC[C@H](c3nsc4ccccc43)CC2)C1] |
| 26 | 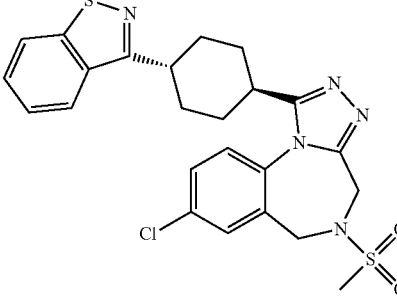 |
| 27 |  |
| 28 | 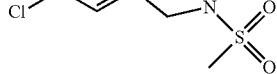 |
| 29 | 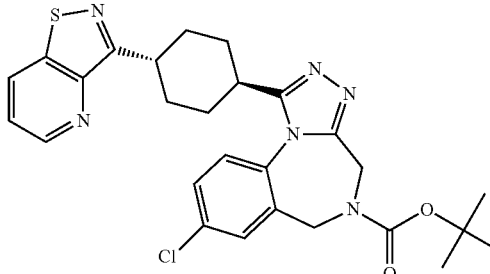 |
| 30 | 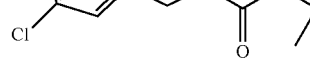 |

TABLE 2-continued structures of selected examples

| Ex | Structure |
|---|---|
| 31 | 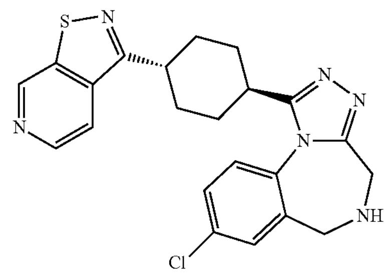 [SMILES: Clc1ccc2c(c1)CNCc1nnc([C@H]3CC[C@H](c4nsc5cnccc54)CC3)n1-2] |
| 32 | 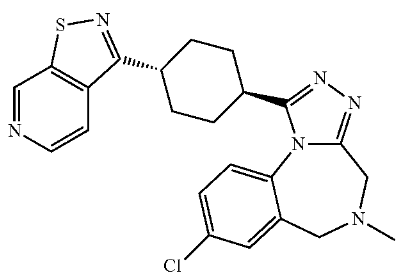 [SMILES: CN1Cc2cc(Cl)ccc2-n2c(nnc2[C@H]2CC[C@H](c3nsc4cnccc43)CC2)C1] |
| 33 | 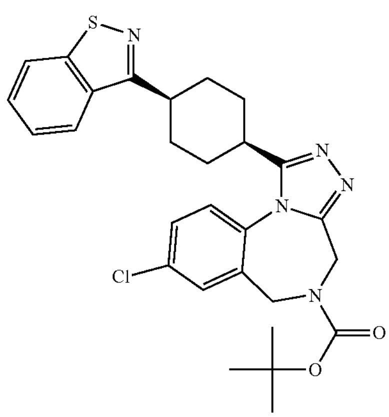 [SMILES: CC(C)(C)OC(=O)N1Cc2cc(Cl)ccc2-n2c(nnc2[C@H]2CC[C@@H](c3nsc4ccccc43)CC2)C1] |
| 34 | 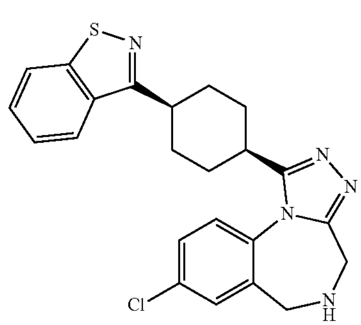 [SMILES: Clc1ccc2c(c1)CNCc1nnc([C@H]3CC[C@@H](c4nsc5ccccc54)CC3)n1-2] |
| 35 | |

A certain embodiment of the invention relates to a compound of formula I, selected from the group consisting of
cis-1-(4-Benzo[d]isoxazol-3-yl-cyclohexyl)-8-chloro-4H,6H-2,3,5,10b-tetraaza-benzo[e]azulene-5-carboxylic acid tert-butyl ester,
trans-1-(4-Benzo[d]isoxazol-3-yl-cyclohexyl)-8-chloro-4H,6H-2,3,5,10b-tetraaza-benzo[e]azulene-5-carboxylic acid tert-butyl ester,
cis-1-(4-Benzo[d]isoxazol-3-yl-cyclohexyl)-8-chloro-5,6-dihydro-4H-2,3,5,10b-tetraaza-benzo[e]azulene,
cis-1-(4-Benzo[d]isoxazol-3-yl-cyclohexyl)-8-chloro-5-methyl-5,6-dihydro-4H-2,3,5,10b-tetraaza-benzo[e]azulene,
trans-1-(4-Benzo[d]isoxazol-3-yl-cyclohexyl)-8-chloro-5,6-dihydro-4H-2,3,5,10b-tetraaza-benzo[e]azulene,
trans-1-(4-Benzo[d]isoxazol-3-yl-cyclohexyl)-8-chloro-5-methyl-5,6-dihydro-4H-2,3,5,10b-tetraaza-benzo[e]azulene,
trans-8-Chloro-1-[4-(6-fluoro-benzo[d]isoxazol-3-yl)-cyclohexyl]-4H,6H-2,3,5,10b-tetraaza-benzo[e]azulene-5-carboxylic acid tert-butyl ester,
trans-8-Chloro-1-[4-(6-fluoro-benzo[d]isoxazol-3-yl)-cyclohexyl]-5,6-dihydro-4H-2,3,5,10b-tetraaza-benzo[e]azulene,
trans-8-Chloro-1-[4-(6-fluoro-benzo[d]isoxazol-3-yl)-cyclohexyl]-5-methyl-5,6-dihydro-4H-2,3,5,10b-tetraaza-benzo[e]azulene,
trans-8-Chloro-1-[4-(5-fluoro-benzo[d]isoxazol-3-yl)-cyclohexyl]-4H,6H-2,3,5,10b-tetraaza-benzo[e]azulene-5-carboxylic acid tert-butyl ester,
trans-8-Chloro-1-[4-(5-fluoro-benzo[d]isoxazol-3-yl)-cyclohexyl]-5,6-dihydro-4H-2,3,5,10b-tetraaza-benzo[e]azulene,
trans-8-Chloro-1-[4-(5-fluoro-benzo[d]isoxazol-3-yl)-cyclohexyl]-5-methyl-5,6-dihydro-4H-2,3,5,10b-tetraaza-benzo[e]azulene,
trans-8-Chloro-1-(4-isoxazolo[4,5-b]pyridin-3-yl-cyclohexyl)-4H,6H-2,3,5,10b-tetraaza-benzo[e]azulene-5-carboxylic acid tert-butyl ester,
trans-8-Chloro-1-(4-isoxazolo[4,5-b]pyridin-3-yl-cyclohexyl)-5,6-dihydro-4H-2,3,5,10b-tetraaza-benzo[e]azulene,
trans-8-Chloro-1-(4-isoxazolo[4,5-b]pyridin-3-yl-cyclohexyl)-5-methyl-5,6-dihydro-4H-2,3,5,10b-tetraaza-benzo[e]azulene,
trans-8-Chloro-1-(4-isoxazolo[5,4-b]pyridin-3-yl-cyclohexyl)-4H,6H-2,3,5,10b-tetraaza-benzo[e]azulene-5-carboxylic acid tert-butyl ester, trans-8-Chloro-1-(4-isoxazolo[5,4-h]pyridin-3-yl-cyclohexyl)-5,6-dihydro-4H-2,3,5,10b-tetraaza-benzo[e]azulene, trans-8-Chloro-1-(4-isoxazolo[5,4-b]pyridin-3-yl-cyclohexyl)-5-methyl-5,6-dihydro-4H-2,3,5,10b-tetraaza-benzo[e]azulene, trans-1-(4-Benzo[d]isothiazol-3-yl-cyclohexyl)-8-chloro-4H,6H-2,3,5,10b-tetraaza-benzo[e]azulene-5-carboxylic acid tert-butyl ester, trans-1-(4-Benzo[d]isothiazol-3-yl-cyclohexyl)-8-chloro-5,6-dihydro-4H-2,3,5,10b-tetraaza-benzo[e]azulene, trans-1-(4-Benzo[d]isothiazol-3-yl-cyclohexyl)-8-chloro-5-methyl-5,6-dihydro-4H-2,3,5,10b-tetraaza-benzo[e]azulene, trans-1-(4-Benzo[d]isothiazol-3-yl-cyclohexyl)-8-chloro-5-cyclobutyl-5,6-dihydro-4H-2,3,5,10b-tetraaza-benzo[e]azulene, trans-{2-[1-(4-Benzo[d]isothiazol-3-yl-cyclohexyl)-8-chloro-4H,6H-2,3,5,10b-tetraaza-benzo[e]azulen-5-yl]-ethyl}-methyl-amine, trans-1-[1-(4-Benzo[d]isothiazol-3-yl-cyclohexyl)-8-chloro-4H,6H-2,3,5,10b-tetraaza-benzo[e]azulen-5-yl]ethanone, trans-1-[1-(4-Benzo[d]isothiazol-3-yl-cyclohexyl)-8-chloro-4H,6H-2,3,5,10b-tetraaza-benzo[e]azulen-5-yl]-2-dimethylamino-ethanone, trans-1-(4-Benzo[d]isothiazol-3-yl-cyclohexyl)-8-chloro-5-methanesulfonyl-5,6-dihydro-4H-2,3,5,10b-tetraaza-benzo[e]azulene, trans-8-Chloro-1-(4-isothiazolo[4,5-b]pyridin-3-yl-cyclohexyl)-4H,6H-2,3,5,10b-tetraaza-benzo[e]azulene-5-carboxylic acid tert-butyl ester, trans-8-Chloro-1-(4-isothiazolo[4,5-b]pyridin-3-yl-cyclohexyl)-5,6-dihydro-4H-2,3,5,10b-tetraaza-benzo[e]azulene, trans-8-Chloro-1-(4-isothiazolo[4,5-b]pyridin-3-yl-cyclohexyl)-5-methyl-5,6-dihydro-4H-2,3,5,10b-tetraaza-benzo[e]azulene, trans-8-Chloro-1-(4-isothiazolo[5,4-c]pyridin-3-yl-cyclohexyl)-4H,6H-2,3,5,10b-tetraaza-benzo[e]azulene-5-carboxylic acid tert-butyl ester, trans-8-Chloro-1-(4-isothiazolo[5,4-c]pyridin-3-yl-cyclohexyl)-5,6-dihydro-4H-2,3,5,10b-tetraaza-benzo[e]azulene, trans-8-Chloro-1-(4-isothiazolo[5,4-c]pyridin-3-yl-cyclohexyl)-5-methyl-5,6-dihydro-4H-2,3,5,10b-tetraaza-benzo[e]azulene, cis-1-(4-Benzo[d]isothiazol-3-yl-cyclohexyl)-8-chloro-4H,6H-2,3,5,10b-tetraaza-benzo[e]azulene-5-carboxylic acid tert-butyl ester, cis-1-(4-Benzo[d]isothiazol-3-yl-cyclohexyl)-8-chloro-5,6-dihydro-4H-2,3,5,10b-tetraaza-benzo[e]azulene, and cis-1-(4-Benzo[d]isothiazol-3-yl-cyclohexyl)-8-chloro-5-methyl-5,6-dihydro-4H-2,3,5,10b-tetraaza-benzo[e]azulene, or a pharmaceutically acceptable salt thereof.

A certain embodiment of the invention relates to a compound of formula I, selected from the group consisting of cis-1-(4-Benzo[d]isoxazol-3-yl-cyclohexyl)-8-chloro-4H,6H-2,3,5,10b-tetraaza-benzo[e]azulene-5-carboxylic acid tort-butyl ester, trans-1-(4-Benzo[d]isoxazol-3-yl-cyclohexyl)-8-chloro-4H,6H-2,3,5,10b-tetraaza-benzo[e]azulene-5-carboxylic acid tert-butyl ester, cis-1-(4-Benzo[c]isoxazol-3-yl-cyclohexyl)-8-chloro-5,6-dihydro-4H-2,3,5,10b-tetraaza-benzo[e]azulene, cis-1-(4-Benzo[d]isoxazol-3-yl-cyclohexyl)-8-chloro-5-methyl-5,6-dihydro-4H-2,3,5,10b-tetraaza-benzo[e]azulene, trans-1-(4-Benzo[d]isoxazol-3-yl-cyclohexyl)-8-chloro-5,6-dihydro-4H-2,3,5,10b-tetraaza-benzo[e]azulene, trans-1-(4-Benzo[d]isoxazol-3-yl-cyclohexyl)-8-chloro-5-methyl-5,6-dihydro-4H-2,3,5,10b-tetraaza-benzo[e]azulene, trans-8-Chloro-1-[4-(6-fluoro-benzo[d]isoxazol-3-yl)-cyclohexyl]-4H,6H-2,3,5,10b-tetraaza-benzo[e]azulene-5-carboxylic acid tert-butyl ester, trans-8-Chloro-1-[4-(6-fluoro-benzo[d]isoxazol-3-yl)-cyclohexyl]-5,6-dihydro-4H-2,3,5,10b-tetraaza-benzo[e]azulene, trans-8-Chloro-1-[4-(6-fluoro-benzo[d]isoxazol-3-yl)-cyclohexyl]-5-methyl-5,6-dihydro-4H-2,3,5,10b-tetraaza-benzo[e]azulene, trans-8-Chloro-1-[4-(5-fluoro-benzo[d]isoxazol-3-yl)-cyclohexyl]-4H,6H-2,3,5,10b-tetraaza-benzo[e]azulene-5-carboxylic acid tert-butyl ester, trans-8-Chloro-1-[4-(5-fluoro-benzo[d]isoxazol-3-yl)-cyclohexyl]-5,6-dihydro-4H-2,3,5,10b-tetraaza-benzo[e]azulene, trans-8-Chloro-1-[4-(5-fluoro-benzo[d]isoxazol-3-yl)-cyclohexyl]-5-methyl-5,6-dihydro-4H-2,3,5,10b-tetraaza-benzo[e]azulene, trans-8-Chloro-1-(4-isoxazolo[4,5-b]pyridin-3-yl-cyclohexyl)-4H,6H-2,3,5,10b-tetraaza-benzo[e]azulene-5-carboxylic acid tert-butyl ester, trans-8-Chloro-1-(4-isoxazolo[4,5-b]pyridin-3-yl-cyclohexyl)-5,6-dihydro-4H-2,3,5,10b-tetraaza-benzo[e]azulene, trans-8-Chloro-1-(4-isoxazolo[4,5-b]pyridin-3-yl-cyclohexyl)-5-methyl-5,6-dihydro-4H-2,3,5,10b-tetraaza-benzo[e]azulene, trans-8-Chloro-1-(4-isoxazolo[5,4-b]pyridin-3-yl-cyclohexyl)-4H,6H-2,3,5,10b-tetraaza-benzo[e]azulene-5-carboxylic acid tert-butyl ester, trans-8-Chloro-1-(4-isoxazolo[5,4-b]pyridin-3-yl-cyclohexyl)-5,6-dihydro-4H-2,3,5,10b-tetraaza-benzo[e]azulene, trans-8-Chloro-1-(4-isoxazolo[5,4-b]pyridin-3-yl-cyclohexyl)-5-methyl-5,6-dihydro-4H-2,3,5,10b-tetraaza-benzo[e]azulene, trans-1-(4-Benzo[d]isothiazol-3-yl-cyclohexyl)-8-chloro-4H,6H-2,3,5,10b-tetraaza-benzo[e]azulene-5-carboxylic acid tert-butyl ester, trans-1-(4-Benzo[d]isothiazol-3-yl-cyclohexyl)-8-chloro-5,6-dihydro-4H-2,3,5,10b-tetraaza-benzo[e]azulene, trans-1-(4-Benzo[d]isothiazol-3-yl-cyclohexyl)-8-chloro-5-methyl-5,6-dihydro-4H-2,3,5,10b-tetraaza-benzo[e]azulene, trans-1-(4-Benzo[d]isothiazol-3-yl-cyclohexyl)-8-chloro-5-cyclobutyl-5,6-dihydro-4H-2,3,5,10b-tetraaza-benzo[d]azulene, trans-{2-[1-(4-Benzo[d]isothiazol-3-yl-cyclohexyl)-8-chloro-4H,6H-2,3,5,10b-tetraaza-benzo[e]azulen-5-yl]-ethyl}-methyl-amine, trans-1-[1-(4-Benzo[c]isothiazol-3-yl-cyclohexyl)-8-chloro-4H,6H-2,3,5,10b-tetraaza-benzo[e]azulen-5-yl]-ethanone, trans-1-[1-(4-Benzo[d]isothiazol-3-yl-cyclohexyl)-8-chloro-4H,6H-2,3,5,10b-tetraaza-benzo[e]azulen-5-yl]-2-dimethylamino-ethanone, trans-1-(4-Benzo[d]isothiazol-3-yl-cyclohexyl)-8-chloro-5-methanesulfonyl-5,6-dihydro-4H-2,3,5,10b-tetraaza-benzo[e]azulene, trans-8-Chloro-1-(4-isothiazolo[4,5-b]pyridin-3-yl-cyclohexyl)-4H,6H-2,3,5,10b-tetraaza-benzo[e]azulene-5-carboxylic acid tert-butyl ester, trans-8-Chloro-1-(4-isothiazolo[4,5-b]pyridin-3-yl-cyclohexyl)-5,6-dihydro-4H-2,3,5,10b-tetraaza-benzo[e]azulene, trans-8-Chloro-1-(4-isothiazolo[4,5-b]pyridin-3-yl-cyclohexyl)-5-methyl-5,6-dihydro-4H-2,3,5,10b-tetraaza-benzo[e]azulene, trans-8-Chloro-1-(4-isothiazolo[5,4-e]pyridin-3-yl-cyclohexyl)-4H,6H-2,3,5,10b-tetraaza-benzo[e]azulene-5-carboxylic acid tert-butyl ester, trans-8-Chloro-1-(4-isothiazolo[5,4-c]pyridin-3-yl-cyclohexyl)-5,6-dihydro-4H-2,3,5,10b-tetraaza-benzo[e]azulene, and trans-8-Chloro-1-(4-isothiazolo[5,4-c]pyridin-3-yl-cyclohexyl)-5-methyl-5,6-dihydro-4H-2,3,5,10b-tetraaza-benzo[e]azulene, or a pharmaceutically acceptable salt thereof.

A certain embodiment of the invention relates to a compound of formula I, selected from the group consisting of trans-1-(4-Benzo[d]isoxazol-3-yl-cyclohexyl)-8-chloro-5,6-dihydro-4H-2,3,5,10b-tetraaza-benzo[e]azulene.HCl, trans-1-(4-Benzo[d]isoxazol-3-yl-cyclohexyl)-8-chloro-5-methyl-5,6-dihydro-4H-2,3,5,10b-tetraaza-benzo[e]azulene, trans-8-Chloro-1-[4-(6-fluoro-benzo[d]isoxazol-3-yl)-cyclohexyl]-5,6-dihydro-4H-2,3,5,10b-tetraaza-benzo[e]azulene.HCl, trans-8-Chloro-1-[4-(6-fluoro-benzo[d]isoxazol-3-yl)-cyclohexyl]-5-methyl-5,6-dihydro-4H-2,3,5,10b-tetraaza-benzo[e]azulene, trans-8-Chloro-1-[4-(5-fluoro-benzo[d]isoxazol-3-yl)-cyclohexyl]-5,6-dihydro-4H-2,3,5,10b-tetraaza-benzo[e]azulene.HCl, trans-8-Chloro-1-[4-(5-fluoro-benzo[d]isoxazol-3-yl)-cyclohexyl]-5-methyl-5,6-dihydro-4H-2,3,5,10b-tetraaza-benzo[e]azulene, trans-8-Chloro-1-(4-isoxazolo[4,5-h]pyridin-3-yl-cyclohexyl)-5,6-dihydro-4H-2,3,5,10b-tetraaza-benzo[e]azulene.HCl, trans-8-Chloro-1-(4-isoxazolo[4,5-b]pyridin-3-yl-cyclohexyl)-5-methyl-5,6-dihydro-4H-2,3,5,10b-tetraaza-benzo[e]azulene, trans-8-Chloro-1-(4-isoxazolo[5,4-b]pyridin-3-yl-cyclohexyl)-5,6-dihydro-4H-2,3,5,10b-tetraaza-benzo[e]azulene.HCl, trans-8-Chloro-1-(4-isoxazolo[5,4-b]pyridin-3-yl-cyclohexyl)-5-methyl-5,6-dihydro-4H-2,3,5,10b-tetraaza-benzo[e]azulene, trans-1-(4-Benzo[d]isothiazol-3-yl-cyclohexyl)-8-chloro-5,6-dihydro-4H-2,3,5,10b-tetraaza-benzo[e]azulene.HCl, trans-1-(4-Benzo[d]isothiazol-3-yl-cyclohexyl)-8-chloro-5-methyl-5,6-dihydro-4H-2,3,5,10b-tetraaza-benzo[e]azulene, trans-1-(4-Benzo[d]isothiazol-3-yl-cyclohexyl)-8-chloro-5-cyclobutyl-5,6-dihydro-4H-2,3,5,10b-tetraaza-benzo[e]azulene, trans-{2-[1-(4-Benzo[d]isothiazol-3-yl-cyclohexyl)-8-chloro-4H,6H-2,3,5,10b-tetraaza-benzo[e]azulen-5-yl]-ethyl}-methyl-amine, trans-1-[1-(4-Benzo[d]isothiazol-3-yl-cyclohexyl)-8-chloro-4H,6H-2,3,5,10b-tetraaza-benzo[e]azulen-5-yl]-ethanone, trans-1-[1-(4-Benzo[d]isothiazol-3-yl-cyclohexyl)-8-chloro-4H,6H-2,3,5,10b-tetraaza-benzo[e]azulen-5-yl]-2-dimethylamino-ethanone, trans-1-(4-Benzo[d]isothiazol-3-yl-cyclohexyl)-8-chloro-5-methanesulfonyl-5,6-dihydro-4H-2,3,5,10b-tetraaza-benzo[e]azulene, trans-8-Chloro-1-(4-isothiazolo[4,5-b]pyridin-3-yl-cyclohexyl)-5,6-dihydro-4H-2,3,5,10b-tetraaza-benzo[e]azulene, trans-8-Chloro-1-(4-isothiazolo[4,5-b]pyridin-3-yl-cyclohexyl)-5-methyl-5,6-dihydro-4H-2,3,5,10b-tetraaza-benzo[e]azulene, trans-8-Chloro-1-(4-isothiazolo[5,4-c]pyridin-3-yl-cyclohexyl)-5,6-dihydro-4H-2,3,5,10b-tetraaza-benzo[e]azulene, and trans-8-Chloro-1-(4-isothiazolo[5,4-c]pyridin-3-yl-cyclohexyl)-5-methyl-5,6-dihydro-4H-2,3,5,10b-tetraaza-benzo[e]azulene, or a pharmaceutically acceptable salt thereof.

A certain embodiment of the invention relates to a compound of formula I, selected from the group consisting of trans-1-(4-Benzo[c]isoxazol-3-yl-cyclohexyl)-8-chloro-5-methyl-5,6-dihydro-4H-2,3,5,10b-tetraaza-benzo[e]azulene, trans-8-Chloro-1-[4-(6-fluoro-benzo[d]isoxazol-3-yl)-cyclohexyl]-5-methyl-5,6-dihydro-4H-2,3,5,10b-tetraaza-benzo[e]azulene, trans-8-Chloro-1-[4-(5-fluoro-benzo[d]isoxazol-3-yl)-cyclohexyl]-5-methyl-5,6-dihydro-4H-2,3,5,10b-tetraaza-benzo[e]azulene, trans-8-Chloro-1-(4-isoxazolo[4,5-b]pyridin-3-yl-cyclohexyl)-5-methyl-5,6-dihydro-4H-2,3,5,10b-tetraaza-benzo[e]azulene, trans-8-Chloro-1-(4-isoxazolo[5,4-b]pyridin-3-yl-cyclohexyl)-5-methyl-5,6-dihydro-4H-2,3,5,10b-tetraaza-benzo[e]azulene, trans-1-(4-Benzo[d]isothiazol-3-yl-cyclohexyl)-8-chloro-5-methyl-5,6-dihydro-4H-2,3,5,10b-tetraaza-benzo[e]azulene, trans-1-(4-Benzo[d]isothiazol-3-yl-cyclohexyl)-8-chloro-5-cyclobutyl-5,6-dihydro-4H-2,3,5,10b-tetraaza-benzo[e]azulene, trans-{2-[1-(4-Benzo[d]isothiazol-3-yl-cyclohexyl)-8-chloro-4H,6H-2,3,5,10b-tetraaza-benzo[e]azulen-5-yl]-ethyl}-methyl-amine, trans-1-[1-(4-Benzo[d]isothiazol-3-yl-cyclohexyl)-8-chloro-4H,6H-2,3,5,10b-tetraaza-benzo[e]azulen-5-yl]-2-dimethylamino-ethanone, trans-8-Chloro-1-(4-isothiazolo[4,5-b]pyridin-3-yl-cyclohexyl)-5-methyl-5,6-dihydro-4H-2,3,5,10b-tetraaza-benzo[e]azulene, and trans-8-Chloro-1-(4-isothiazolo[5,4-c]pyridin-3-yl-cyclohexyl)-5-methyl-5,6-dihydro-4H-2,3,5,10b-tetraaza-benzo[e]azulene, or a pharmaceutically acceptable salt thereof.

A certain embodiment of the invention relates to a compound as described in any of the embodiments obtainable by a process according as described herein.

A certain embodiment of the invention relates to a compound as described in any of the embodiments, whenever obtainable by a process according as described herein.

A certain embodiment of the invention relates to a compound as described in any of the embodiments for the use as therapeutically active substance.

A certain embodiment of the invention relates to a compound as described in any of the embodiments for a use in the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention relates to a pharmaceutical composition comprising a compound as described in any of the embodiments.

A certain embodiment of the invention relates to a pharmaceutical composition comprising a compound as described in any of the embodiments, wherein it is useful for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention relates to the use of a compound as described in any of the embodiments for the preparation of a medicament.

A certain embodiment of the invention relates to the use of a compound as described in any of the embodiments for the preparation of a medicament, wherein the medicament is useful for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention relates to the use of a compound as described in any of the embodiments for the prevention or treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior.

A certain embodiment of the invention relates to a method for the therapeutic and/or prophylactic treatment of dysmenorrhea, male or female sexual dysfunction, hypertension, chronic heart failure, inappropriate secretion of vasopressin, liver cirrhosis, nephrotic syndrome, anxiety, depressive disorders, obsessive compulsive disorder, autistic spectrum disorders, schizophrenia, and aggressive behavior, which method comprises administering a compound as defined in any if the embodiments to a human being or animal.

In a certain embodiment, the compounds of formula I of the invention can be manufactured according to a process comprising the step of reacting a compound of formula II

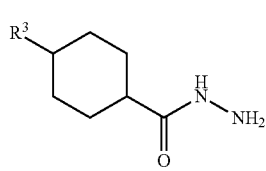

II with a compound of formula III

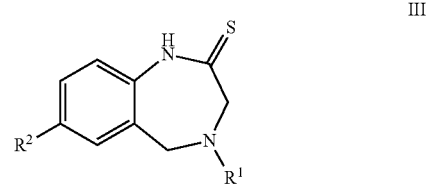

III to obtain a compound of formula I wherein $R^1$, $R^2$ and $R^3$ are as defined hereinabove for formula I.

The processes are described in more detail with the following general schemes and procedures A to F.

Scheme 1: General Scheme A

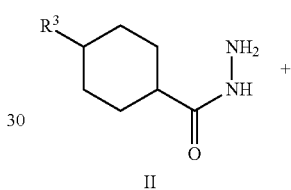

II

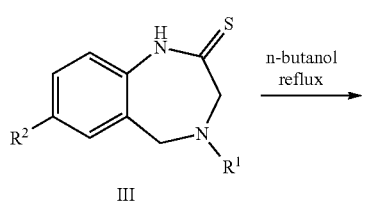

III

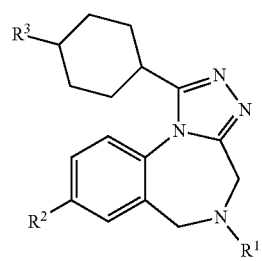

I

Compounds of formula I can be prepared by thermal condensation of a hydrazide of formula II and a thiolactam of formula III. The synthesis of compounds of formula II is outlined in general schemes D-F hereinafter. Compounds of formula III can be prepared following the procedures described in general scheme C as described hereinafter. General scheme A is hereinafter further illustrated with general procedure VIII.

Scheme 2: General Scheme B

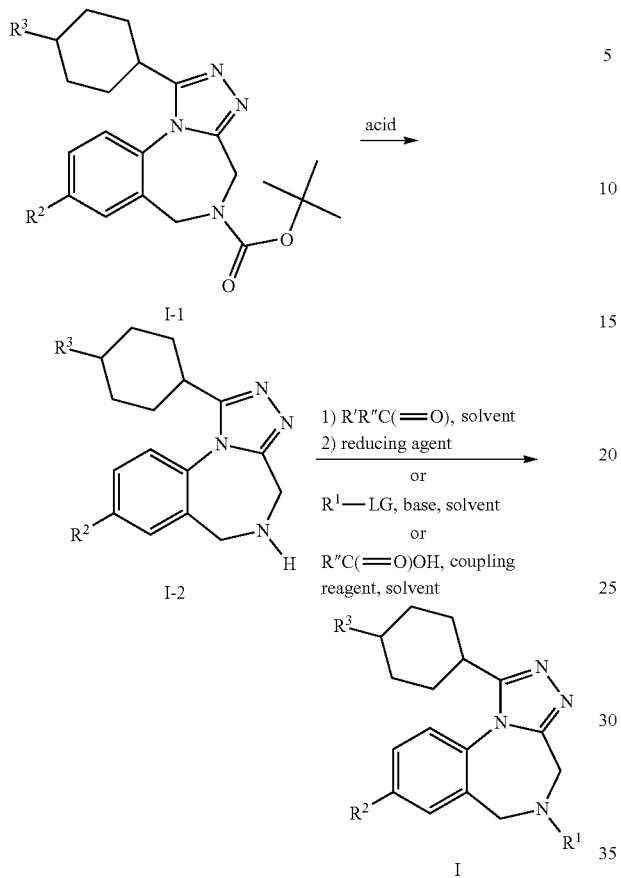

R' = H, $C_a$-alkyl, optionally substituted,
R" = $C_b$-alkyl, optionally substituted,
or R' and R" form together an optionally
substituted cycloalkyl, and a + b are </ = 5.

Compounds of formula I with $R^1$ different from H can be prepared from compounds of formula I-2 (compounds of formula I wherein $R^1$ is H) according to methods known in the art, e.g. by treating a compound of formula I-2 with an inorganic base such as a carbonate salt or an organic base such as a tertiary amine and an electrophilic reactant $R^1$-LG (wherein LG is a leaving group like. halogen or sulfonyl) which is either commercially available or easily prepared according to methods and starting materials well known in the art. Alternatively, compounds of formula I can be obtained via reductive alkylation by consecutively treating a compound of formula I-2 with a ketone or aldehyde and a suitable reducing agent like a borohydride derivative such as sodium borohydride, sodium cyanoborohydride or sodium triacetoxyborohydride. Alternatively, compounds of formula I, in which $R^1$ is an acyl group, can be manufactured by coupling an amine of formula I-2 with a carboxylic acid. The usual reagents and protocols known in the art can be used to effect the amide coupling. Compounds of formula I-2 can be obtained by cleavage of the substituent $R^1$ of a compound of formula I using methods known in the art. Compounds of formula I-2 are conveniently obtained as the salt or the free base after basic aqueous work-up by treatment of compounds of formula I-1 (compounds of formula I in which $R^1$ is tert-butoxycarbonyl) with an acid in a suitable solvent like methanesulphonic acid in dichloromethane or tetrahydrofuran or hydrochloric acid in methanol. General scheme B is hereinafter further illustrated with general procedures IX and X.

Scheme 3: General Scheme C

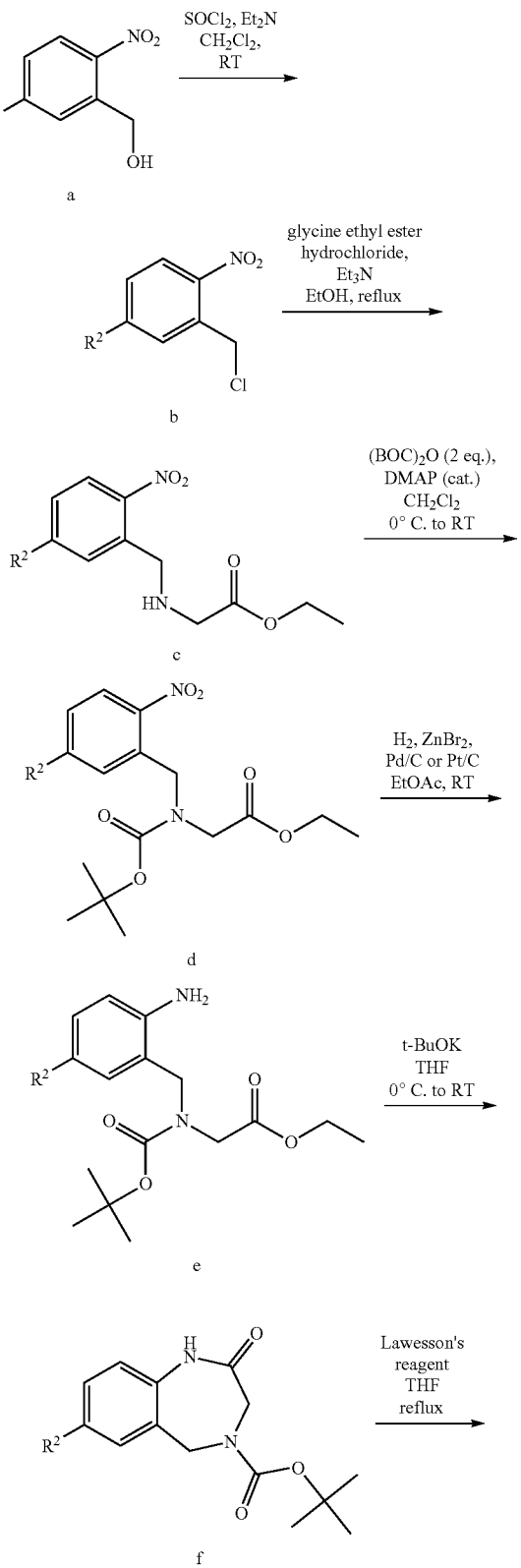

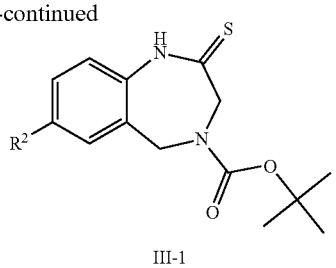

III-1

A thiolactam of formula III-1 (compounds of formula III in which $R^1$ is tert-butoxycarbonyl) can be obtained as follows: Transformation of a 2-nitrobenzyl alcohol of formula a to a benzylic chloride of formula b can be affected by a chlorinating reagent such as thionyl chloride in the presence of an organic tertiary amine base. Alkylation of a compound of formula b with glycine ethyl ester hydrochloride in the presence of an organic tertiary amine base and N-protection of the resulting compound of formula c using di-tert-butyl dicarbonate and a catalytic amount of 4-N,N-dimethylaminopyridine gives compounds of formula d. The nitro group can be reduced selectively by hydrogenation over palladium or platinum on charcoal, which has been pretreated with a zinc halide such as zinc bromide, to give aniline intermediates of formula e. Cyclization to lactams of formula f is achieved by treatment of compounds of formula e with a suitable base, e.g. potassium tert-butoxide, in tetrahydrofuran. A thiolactam of formula III-1 is obtained by treatment of a compound of formula f with Lawesson's reagent or phosphorous pentasulphide at elevated temperature.

Scheme 4: General Scheme D

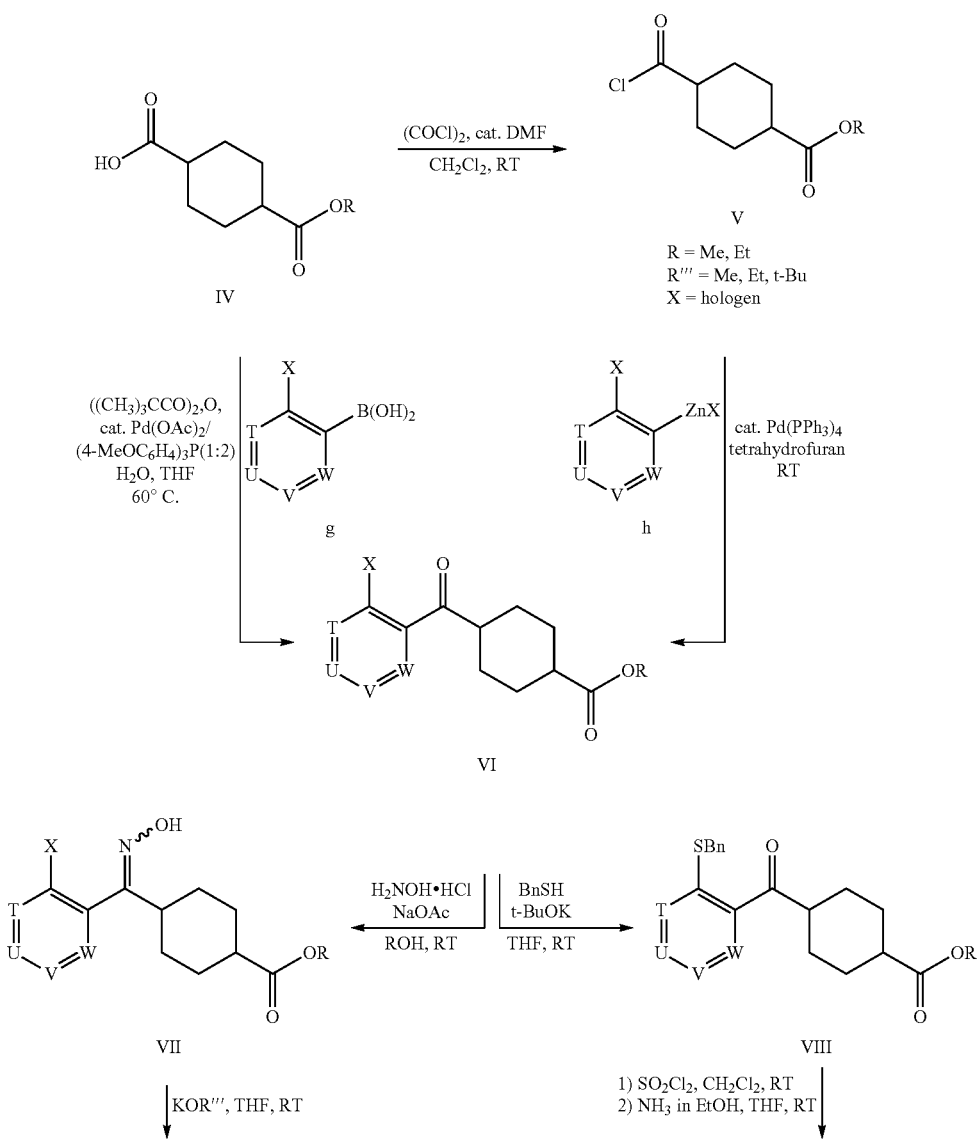

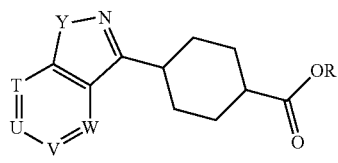
IX-1 (Y = O)

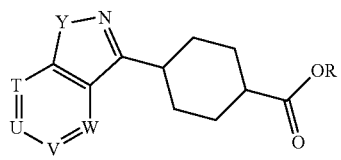
IX-2 (Y = S)

T, U, V, W = C-Ra or N, with Ra = H, OH, halogen, cyano, C1-6-alkyl, C1-6-alkoxy, halogen-C1-6-alkyl, halogen-C1-6-alkoxy or hydroxy-C1-6-alkyl 4-Aroyl-cyclohexanecarboxylic acid ester intermediates of formula VI can be prepared by coupling a cyclohexane-1,4-dicarboxylic acid monoester of formula IV with an aryl or heteroaryl boronic acid of formula g in the presence of a carboxylic acid anhydride such as trimethylacetic anhydride and a suitable palladium catalyst such as a mixture of palladium(II) acetate and a phosphine ligand, e.g. tris(4-methoxyphenyl)phosphine, in tetrahydrofuran containing a small amount of water at 60° C. Alternatively, 4-aroyl-cyclohexanecarboxylic acid ester intermediates of formula VI can be synthesized by coupling a 4-chlorocarbonyl-cyclohexanecarboxylic acid ester of formula V, which can be obtained from a cyclohexane-1,4-dicarboxylic acid monoester of formula IV by methods known in the art for the conversion of carboxylic acids to carboxylic acid chlorides such as treatment with thionyl chloride or oxalyl chloride and a catalytic amount of N,N-dimethylformamide, with an aryl or heteroaryl zinc halide of formula h in the presence of a suitable palladium catalyst such as tetrakis(triphenylphosphine)palladium(0) in tetrahydrofuran at room temperature. Treatment of a 4-aroyl-cyclohexanecarboxylic acid ester intermediate of formula VI with a mixture of hydroxylamine hydrochloride and sodium acetate in a suitable alcohol at room temperature gives rise to an oxime intermediate of formula VII, which is usually obtained as an E/Z mixture. An oxime intermediate of formula VII can be cyclized to an aryl or heteroaryl isoxazole intermediate of formula IX-1 by treatment with a potassium alkoxide base in tetrahydrofuran at room temperature. Alternatively, treatment of a 4-aroyl-cyclohexanecarboxylic acid ester intermediate of formula VI with benzyl mercaptane and potassium tert-butoxide in tetrahydrofuran at room temperature leads to a benzyl ether of formula VIII, which can be cyclized to an aryl or heteroaryl isothiazole intermediate of formula IX-2 via consecutive S-debenzylation with sulfuryl chloride in dichloromethane at room temperature and treatment with an ethanolic solution of ammonia in tetrahydrofuran at room temperature. General scheme D is hereinafter further illustrated with general procedures I to V.

Scheme 5: General Scheme E

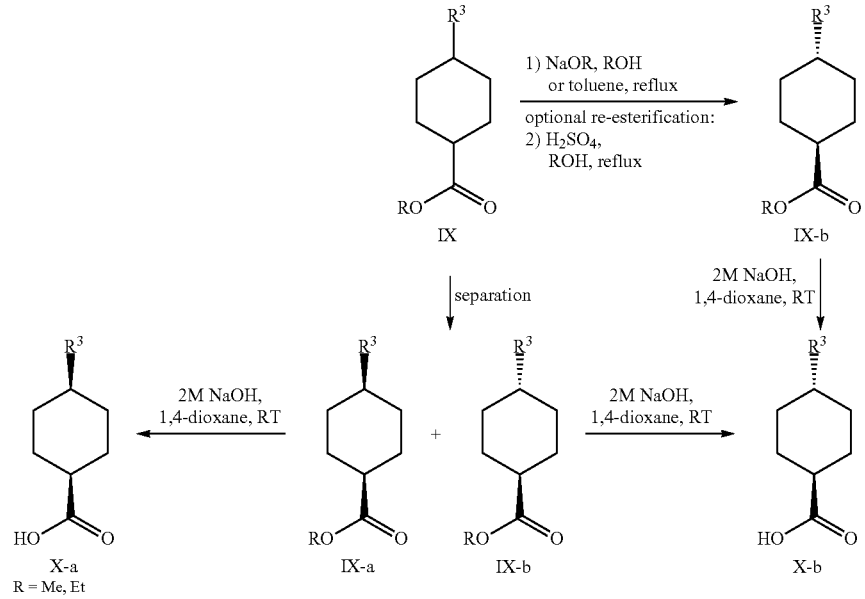

Cis/trans mixtures of 4-heteroaryl-cyclohexane carboxylic acid ester intermediates of formula IX can in some cases be separable by the usual methods such as silica gel column or high performance chromatography or crystallization into pure cis-4-heteroaryl-cyclohexane carboxylic acid ester intermediates of formula IX-a and trans-4-heteroaryl-cyclohexane carboxylic acid ester intermediates of formula IX-b, which can be saponified to pure cis-4-heteroaryl-cyclohexane carboxylic acid intermediates of formula X-a and trans-4-heteroaryl-cyclohexane carboxylic acid intermediates of formula X-b under standard conditions such as stirring in a mixture of aqueous sodium hydroxide solution and an etheral solvent such as 1,4-dioxane, tetrahydrofuran or diethyl ether a room temperature. Alternatively, trans-4-heteroaryl-cyclohexane carboxylic acid intermediates of formula X-b can be obtained by epimerization of the cis isomer of cis/trans-mixtures of 4-heteroaryl-cyclohexane carboxylic acid ester intermediates of formula IX using a suitable base, e.g. an alkali metal alkoxide such as sodium or potassium methylate or ethylate, in a suitable solvent such as methanol, ethanol or toluene at reflux followed by saponification of the crude reaction mixture, which can consist of a mixture of a trans-4-heteroaryl-cyclohexane carboxylic acid intermediate of formula X-b and a trans-4-heteroaryl-cyclohexane carboxylic acid ester intermediate of formula IX-b, under standard conditions such as stirring in a mixture of aqueous sodium hydroxide solution and an etheral solvent such as 1,4-dioxane, tetrahydrofuran or diethyl ether at room temperature. In case the epimerization reaction was carried out in an alcohol as solvent, the crude reaction mixture can alternatively be acidified by the addition of concentrated sulfuric acid and heated to reflux to obtain a trans-4-heteroaryl-cyclohexane carboxylic acid ester intermediate of formula IX-b.

Scheme 6: General Scheme F

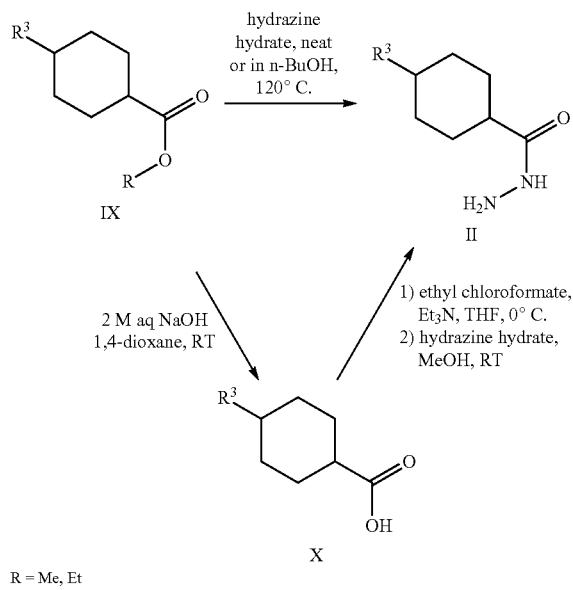

R = Me, Et

A 4-heteroaryl-cyclohexanecarboxylic acid ester intermediate of formula IX can be converted to a hydrazide of formula II by heating with hydrazine hydrate. Alternatively, an ester of formula IX can be hydrolyzed to a carboxylic acid of formula X using a biphasic mixture of aqueous sodium or potassium hydroxide solution and an etheral solvent such as dioxane, tetrahydrofuran or diethyl ether. A hydrazide of formula II can be obtained by activating an acid intermediate of formula X, e.g. with ethyl chloroformate, thionyl chloride, oxalylchloride or a peptide coupling reagent, and subsequent coupling with hydrazine. General scheme F is hereinafter further illustrated with general procedures VI and VII.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula as well as all intermediate products can be prepared according to analogous methods or according to the methods set forth herein. Starting materials are commercially available, known in the art or can be prepared by methods known in the art or in analogy thereto.

It will be appreciated that the compounds of formula I in this invention can be derivatized at functional groups to provide derivatives which are capable of conversion back to the parent compound in vivo.

Pharmacological Tests

The compounds of the present invention exhibit V1a activity. They are selective inhibitors of the V1a receptor and are therefore likely to have a low potential to cause unwanted off-target related side-effects. The V1a activity can be detected as described below.

The human V1a receptor was cloned by RT-PCR from total human liver RNA. The coding sequence was subcloned in an expression vector after sequencing to confirm the identity of the amplified sequence. To demonstrate the affinity of the compounds from the present invention to the human V1a receptor binding studies were performed. Cell membranes were prepared from HEK293 cells transiently transfected with the expression vector and grown in 20 liter fermenters with the following protocol.

50 g of cells are resuspended in 30 ml freshly prepared ice cold Lysis buffer (50 mM HEPES, 1 mM EDTA, 10 mM magnesium dichloride adjusted to pH=7.4+complete cocktail of protease inhibitor (Roche Diagnostics)). Homogenized with Polytron for 1 min and sonicated on ice for 2×2 minutes at 80% intensity (Vibracell sonicator). The preparation is centrifuged 20 min at 500 g at 4° C., the pellet is discarded and the supernatant centrifuged 1 hour at 43'000 g at 4° C. (19'000 rpm). The pellet is resuspended in 12.5 ml Lysis buffer+12.5 ml sucrose 20% and homogenized using a Polytron for 1-2 min. The protein concentration is determined by the Bradford method and aliquots are stored at −80° C. until use. For binding studies 60 mg Yttrium silicate SPA beads (Amersham®) are mixed with an aliquot of membrane in binding buffer (50 mM Tris, 120 mM sodium chloride, 5 mM potassium chloride, 2 mM calcium dichloride, 10 mM magnesium dichloride) for 15 minutes with mixing. 50 µl of bead/membrane mixture is then added to each well of a 96 well plate, followed by 50 µl of 4 nM 3H-Vasopressin (American Radiolabeled Chemicals). For total binding measurement 100 µl of binding buffer are added to the respective wells, for non-specific binding 100 µl of 8.4 mM cold vasopressin and for compound testing 100 µl of a serial dilution of each compound in 2% dimethyl sulfoxide. The plate is incubated 1 h at room temperature, centrifuged 1 min at 1000 g and counted on a Packard Top-Count. Non-specific binding counts are subtracted from each well and data is normalized to the maximum specific binding set at 100%. To calculate an $IC_{50}$ the curve is fitted using a non-linear regression model (XLfit) and the Ki is calculated using the Cheng-Prussoff equation.

The following representative data show the antagonistic activity against human V1a receptor of compounds according to present invention.

TABLE 3 human V1a pKi of selected examples

| Ex# | pKi (hV1a) |
|---|---|
| 1 | 8.05 |
| 2 | 8.32 |
| 3 | 7.95 |
| 4 | 8.12 |
| 5 | 9.05 |
| 6 | 9.10 |
| 7 | 8.32 |
| 8 | 8.82 |
| 9 | 8.92 |
| 10 | 8.49 |
| 11 | 8.68 |
| 12 | 9.10 |
| 13 | 8.57 |
| 14 | 8.66 |
| 15 | 9.15 |
| 16 | 8.44 |
| 17 | 8.28 |
| 18 | 9.05 |
| 19 | 8.12 |
| 20 | 8.82 |
| 21 | 8.80 |
| 22 | 9.52 |
| 23 | 9.22 |
| 24 | 9.40 |
| 25 | 9.52 |
| 26 | 9.52 |
| 27 | 8.37 |
| 28 | 8.96 |
| 29 | 9.10 |
| 30 | 8.26 |
| 31 | 8.59 |
| 32 | 9.05 |
| 33 | 8.96 |
| 34 | 7.59 |
| 35 | 8.37 |

Pharmaceutical Compositions

The compounds of formula I as well as their pharmaceutically acceptable salts can be used as therapeutics, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injectable solutions.

The compounds of formula I and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc.

Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

Examples of compositions according to the invention are, but are not limited to:

Example A

Tablets of the Following Composition are Manufactured in the Usual Manner

TABLE 4 possible tablet composition

| | mg/tablet | | | |
|---|---|---|---|---|
| ingredient | 5 | 25 | 100 | 500 |
| 1. compound of formula I | 5 | 25 | 100 | 500 |
| 2. lactose | 45 | 105 | 30 | 150 |
| 3. corn starch | 15 | 6 | 6 | 60 |
| 4. microcrystalline cellulose | 34 | 30 | 30 | 450 |
| 5. magnesium stearate | 1 | 1 | 1 | 1 |
| total | 100 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the Following Composition are Manufactured

TABLE 5 possible capsule ingredient composition

| | mg/capsule | | | | |
|---|---|---|---|---|---|
| ingredient | 5 | 10 | 25 | 100 | 500 |
| 1. compound of formula I | 5 | 10 | 25 | 100 | 500 |
| 2. lactose | 159 | 155 | 123 | 148 | — |
| 3. corn starch | 25 | 30 | 35 | 40 | 70 |
| 4. talc | 10 | 5 | 15 | 10 | 25 |
| 5. magnesium stearate | 1 | — | 2 | 2 | 5 |
| total | 200 | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer, the talc (and magnesium stearate) is added thereto and mixed thoroughly. The mixture is filled by machine into suitable capsules, e.g. hard gelatin capsules.

Example B-2

Soft Gelatin Capsules of the Following Composition are Manufactured

TABLE 6 possible soft gelatin capsule ingredient composition

| ingredient | mg/capsule |
| --- | --- |
| compound of formula I | 5 |
| yellow wax | 8 |
| hydrogenated soybean oil | 8 |
| partially hydrogenated plant oils | 34 |
| soybean oil | 110 |
| total | 165 |

TABLE 7 possible soft gelatin capsule composition

| ingredient | mg/capsule |
| --- | --- |
| gelatin | 75 |
| glycerol 85% | 32 |
| karion 83 | 8 (dry matter) |
| titanium dioxide | 0.4 |
| iron oxide yellow | 1.1 |
| total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

Example C

Suppositories of the Following Composition are Manufactured

TABLE 8 possible suppository composition

| ingredient | mg/supp. |
| --- | --- |
| compound of formula I | 15 |
| suppository mass | 1285 |
| total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection Solutions of the Following Composition are Manufactured

TABLE 9 possible injection solution composition

| ingredient | mg/injection solution. |
| --- | --- |
| compound of formula I | 3 |
| polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the Following Composition are Manufactured

TABLE 10 possible sachet composition

| ingredient | mg/sachet |
| --- | --- |
| compound of formula I | 50 |
| lactose, fine powder | 1015 |
| microcrystalline cellulose (AVICEL PH 102) | 1400 |
| sodium carboxymethyl cellulose | 14 |
| polyvinylpyrrolidon K 30 | 10 |
| magnesium stearate | 10 |
| flavoring additives | 1 |
| total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXAMPLES

The following examples are provided for illustration of the invention. They should not be considered as limiting the scope of the invention, but merely as being representative thereof.

Intermediate of Formula (V)

trans-4-Chlorocarbonyl-cyclohexanecarboxylic acid methyl ester

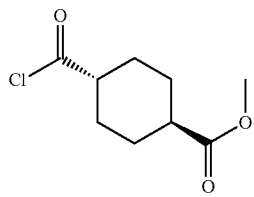

To a solution of trans-1,4-cycloxanedicarboxylic acid monomethylester (2.0 g, 11 mmol) in dichloromethane (30 ml) was added oxalyl chloride (1.1 ml, 13 mmol) and a catalytic amount of N,N-dimethylformamide at 0-5°. The cooling bath was removed, and the reaction mixture was stirred for 24 h at room temperature. After evaporation of the solvent the residue was triturated in n-hexane (100 ml). The precipitate was removed by filtration. The filtrate was concentrated in vacuo to give the title compound (2.2 g, quantitative) as colorless oil which was used in the next step without further purification.

4-Aroyl-cyclohexanecarboxylic acid ester intermediates of formula VI

General Procedure (I): Negishi Coupling

To a solution of an aryl or heteroaryl bromide (1 eq) in dry tetrahydrofuran (0.2 M) is added a 2M isopropyl magnesium chloride solution in tetrahydrofuran (1.05 eq) at 0-5° C. The cooling bath is removed and the reaction mixture is stirred for 1 h at room temperature. A solution of zinc chloride (2 eq), which is previously dried by melting in vacuo followed by cooling under argon, in dry tetrahydrofuran (1.0 M) is added to the Grignard intermediate. Stirring for 1 h is followed by addition of 4-chlorocarbonyl-cyclohexanecarboxylic acid methyl ester (1 eq) and tetrakis(triphenylphosphine)palladium(0) (0.05 eq). The reaction mixture is quenched with aqueous saturated ammonium chloride solution after 18-24 h and extracted with two or three portions of an organic solvent such as tert-butyl methyl ether or ethyl acetate. The combined organic layers are dried over anhydrous sodium sulfate and concentrated to dryness. Purification by flash-chromatography gives 4-aroyl-cyclohexanecarboxylic acid ester intermediate of formula VI.

4-Aroyl-cyclohexanecarboxylic acid ester 1 trans-4-(2-Fluoro-benzoyl)-cyclohexanecarboxylic acid methyl ester

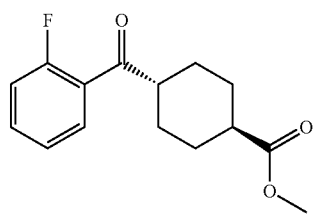 [SMILES: COC(=O)[C@H]1CC[C@H](C(=O)c2ccccc2F)CC1]

The title compound was obtained as colorless liquid in 32% yield from 1-bromo-2-fluorobenzene according to general procedure (I). MS m/e: 264 (M$^+$)

4-Aroyl-cyclohexanecarboxylic acid ester 2 cis/trans-4-(2-Fluoro-benzoyl)-cyclohexanecarboxylic acid methyl ester (2:1)

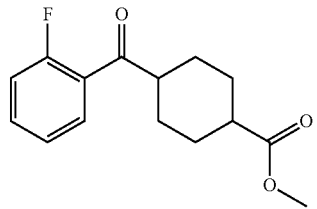 [SMILES: COC(=O)C1CCC(C(=O)c2ccccc2F)CC1]

A solution of cis/trans-1,4-cycloxanedicarboxylic acid monomethyl ester (2.0 g, 11 mmol), 2-fluorophenylboronic acid (2.0 g, 14 mmol), tris(4-methoxyphenyl)phosphine (0.76 g, 2.1 mmol) and palladium(II) acetate (0.24 g, 1.1 mmol) in tetrahydrofuran (50 ml) and water (0.48 ml, 27 mmol) was purged with argon. Addition of trimethylacetic anhydride (3.3 ml, 16 mmol) was followed by stirring at 60° C. for 20 h. After cooling to room temperature palladium precipitations were removed by filtration over Decalite®. The solvent was evaporated. The residue was partitioned between ethyl acetate (200 ml) and 1M aqueous sodium carbonate solution (100 ml). The layers were separated. The organic layer was washed with one 100-ml portion of 2M aqueous sodium carbonate solution. The combined aqueous layers were extracted with one 100-ml portion of ethyl acetate. The combined organic layers were dried over anhydrous sodium sulfate and concentrated to dryness. Purification by flash-chromatography with n-heptane/ethyl acetate as eluent gave the title compound (0.52 g, 18%) as colorless oil.

4-Aroyl-cyclohexanecarboxylic acid ester 3 trans-4-(2,4-Difluoro-benzoyl)-cyclohexanecarboxylic acid methyl ester

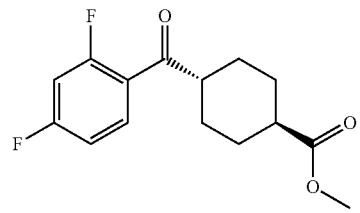 [SMILES: COC(=O)[C@H]1CC[C@H](C(=O)c2ccc(F)cc2F)CC1]

The title compound was obtained as white solid in 93% yield from 1-bromo-2,4-difluorobenzene according to general procedure (I). MS m/e: 282 (M⁺)

4-Aroyl-cyclohexanecarboxylic acid ester 4 trans-4-(2,5-Difluoro-benzoyl)-cyclohexanecarboxylic acid methyl ester

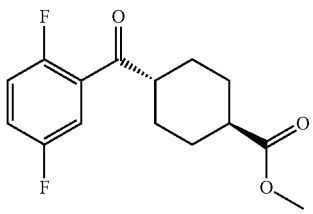 [SMILES: COC(=O)[C@H]1CC[C@H](C(=O)c2cc(F)ccc2F)CC1]

The title compound was obtained as colorless oil in 55% yield from 1-bromo-2,5-difluorobenzene according to general procedure (I). MS m/e: 282 (M⁻)

4-Aroyl-cyclohexanecarboxylic acid ester 5 trans-4-(3-Fluoro-pyridine-2-carbonyl)-cyclohexanecarboxylic acid methyl ester

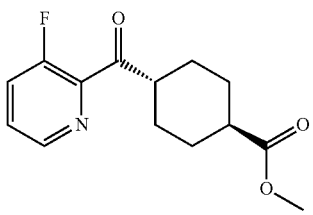 [SMILES: COC(=O)[C@H]1CC[C@H](C(=O)c2ncccc2F)CC1]

and

4-Aroyl-cyclohexanecarboxylic acid ester 6 trans-4-(3-Fluoro-pyridine-4-carbonyl)-cyclohexanecarboxylic acid methyl ester

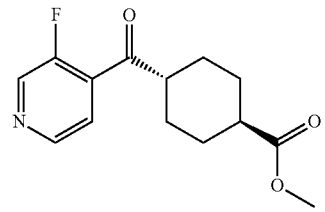 [SMILES: COC(=O)[C@H]1CC[C@H](C(=O)c2ccncc2F)CC1]

To a solution of N,N,N'N'-tetramethylethylenediamine (1.20 g, 10.3 mmol) in diethyl ether (50 ml) at −78° C. was added 1.6M N-butyl lithium solution in n-hexane (6.40 ml, 10.3 mmol). Stirring for 1 h at −20° C. was followed by addition of 3-fluoropyridine (1.00 g, 10.3 mmol) at −78° C. After stirring at −60 to −70° C. for 3 h a solution of zinc chloride (2.81 g, 20.6 mmol), which had previously been dried by melting in vacuo followed by cooling under argon, in diethyl ether (20 ml) was added dropwise at max. −60° C. The reaction mixture was allowed to warm to room temperature 45 minutes after completed addition. Addition of tetrakis(triphenylphosphine)palladium(0) (0.59 g, 0.51 mmol) and trans-4-chlorocarbonyl-cyclohexanecarboxylic acid methyl ester (2.10 g, 10.3 mmol) was followed by stirring for 16 h. The reaction was quenched with aqueous saturated ammonium chloride solution and the mixture was extracted with three 100-ml portions of tert-butyl methyl ether. The combined organic layers were washed with one 50-ml portion of 2 M aqueous sodium carbonate solution and one 50-ml portion of brine, dried over anhydrous sodium sulfate and concentrated to dryness. Separation by flash-chromatography with n-heptane/ethyl acetate as eluent gave trans-4-(3-fluoro-pyridine-2-carbonyl)-cyclohexanecarboxylic acid methyl ester (0.22 g, 7.9%) as yellow oil and trans-4-(3-fluoro-pyridine-4-carbonyl)-cyclohexanecarboxylic acid methyl ester (0.23 g, 8.4%) as yellow solid.

trams-4-(3-Fluoro-pyridine-2-carbonyl)-cyclohexanecarboxylic acid methyl ester. MS m/e: 266 ([M+H]⁺)
trans-4-(3-Fluoro-pyridine-4-carbonyl)-cyclohexanecarboxylic acid methyl ester. MS m/e: 266 ([M+H]⁺)

4-Aroyl-cyclohexanecarboxylic acid ester 7 trans-4-(2-Chloro-pyridine-3-carbonyl)-cyclohexanecarboxylic acid methyl ester

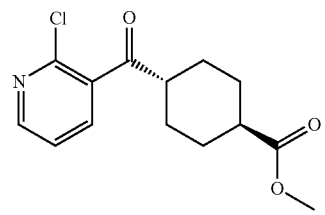 [SMILES: COC(=O)[C@H]1CC[C@H](C(=O)c2cccnc2Cl)CC1]

To a mixture of lithium chloride (0.55 g, 13 mmol) and magnesium turnings (0.63 g, 26 mmol) in dry tetrahydrofuran (34 ml) was added 1M diisobutyl aluminum hydride solution in tetrahydrofuran (0.10 ml, 0.10 mmol) at room temperature. After stirring for 5 minutes a solution of 3-bromo-2-chloro-pyridine (2.00 g, 10.4 mmol) in dry tetrahydrofuran (1 ml) was added at 0-5° C. Stirring for 1 h was followed by addition of a solution of zinc chloride (1.42 g, 10.4 mmol), which had previously been dried by melting in vacuo followed by cooling under argon, in dry tetrahydrofuran (10 ml). After stirring for 1 h the mixture was decanted into another flask by cannulation under argon. Addition of tetrakis(triphenylphosphine)palladium(0) (0.59 g, 0.51 mmol) and trans-4-chlorocarbonyl-cyclohexanecarboxylic acid methyl ester (2.10 g, 10.3 mmol) was followed by stirring at room temperature for 18 h. The mixture was partitioned between ethyl acetate (150 ml) and 0.1M aqueous hydrogen chloride solution (100 ml). The layers were separated. The aqueous layer was extracted with two 100-ml portions of ethyl acetate. The combined organic layers were dried over anhydrous sodium sulfate and concentrated to dryness. Purification by flash-chromatography with n-heptane/tert-butyl methyl ether as eluent gave the title compound (1.3 g, 46%) as yellow solid. MS m/e: 282 ([M+H]$^+$)

Oxime Intermediates of Formula (VII)

General Procedure (II): Oxime Formation

A mixture of a 4-aroyl-cyclohexanecarboxylic acid ester of formula VI (1 eq), sodium acetate (2.4 eq) and hydroxylamine hydrochloride (2.4 eq) in an alcohol such as methanol or ethanol (0.1-0.2 M) is stirred at room temperature for 2-24 h. The reaction mixture is optionally concentrated to dryness or directly partitioned between an organic solvent such as ethyl acetate or tert-butyl methyl ether and 2M aqueous sodium carbonate solution. The layers are separated. The aqueous layer is extracted with one or two portions of organic solvent. The combined organic layers are dried over anhydrous sodium sulfate and concentrated to dryness. Purification by flash-chromatography gives an oxime intermediate of formula VII.

Oxime 1 cis/trans-4-{(2-Fluoro-phenyl)-[(E/Z)-hydroxy-imino]-methyl}-cyclohexanecarboxylic acid methyl ester

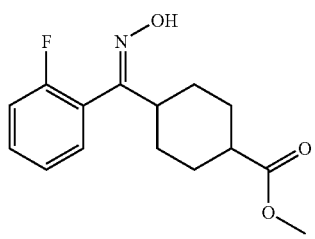 [SMILES: COC(=O)C1CCC(/C(=N\O)c2ccccc2F)CC1]

The title compound was obtained as white solid in 98% yield from cis/trans-4-(2-fluoro-benzoyl)-cyclohexanecarboxylic acid methyl ester (2:1) according to general procedure (II). MS m/e: 280 ([M+H]$^+$)

Oxime 2 trans-4-{(2,4-Difluoro-phenyl)-[(E/Z)-hydroxy-imino]-methyl}-cyclohexanecarboxylic acid methyl ester

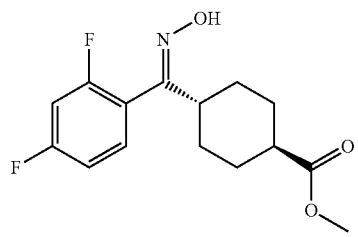 [SMILES: COC(=O)[C@H]1CC[C@H](/C(=N\O)c2ccc(F)cc2F)CC1]

The title compound was obtained as off-white solid in 97% yield from trans-4-(2,4-difluoro-benzoyl)-cyclohexanecarboxylic acid methyl ester according to general procedure (II). MS m/e: 298 ([M+H]$^+$)

Oxime 3 trans-4-{(2,5-Difluoro-phenyl)-[(E/Z)-hydroxy-imino]-methyl}-cyclohexanecarboxylic acid methyl ester

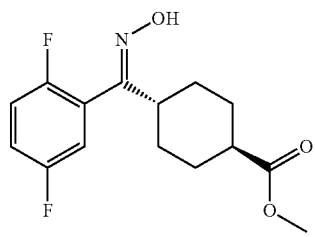 [SMILES: COC(=O)[C@H]1CC[C@H](/C(=N\O)c2cc(F)ccc2F)CC1]

The title compound was obtained as off-white solid in 97% yield from trans-4-(2,5-difluoro-benzoyl)-cyclohexanecarboxylic acid methyl ester according to general procedure (II). MS m/e: 298 ([M+H]$^+$)

Oxime 4 trans-4-{(3-Fluoro-pyridin-2-yl)-([E/Z]-hydroxy-imino]-methyl}-cyclohexanecarboxylic acid methyl ester

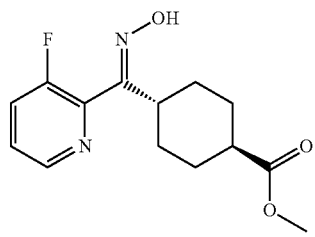 [SMILES: COC(=O)[C@H]1CC[C@H](/C(=N\O)c2ncccc2F)CC1]

The title compound was obtained as off-white solid in 97% yield from trans-4-(3-fluoro-pyridine-2-carbonyl)-cyclohexanecarboxylic acid methyl ester according to general procedure (II). MS m/e: 281 ([M+H]$^+$)

Oxime 5 trans-4-{(2-Chloro-pyridin-3-yl)-[(E/Z)-hydroxyimino]-methyl}-cyclohexanecarboxylic acid methyl ester

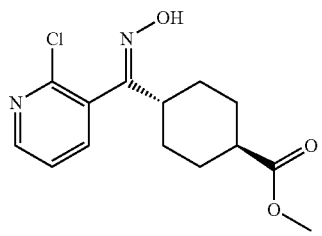 [SMILES: COC(=O)[C@H]1CC[C@H](/C(=N\O)c2cccnc2Cl)CC1]

The title compound was obtained as orange solid in 92% yield from trans-4-(2-chloro-pyridine-3-carbonyl)-cyclohexanecarboxylic acid methyl ester according to general procedure (II). MS m/e: 297 ([M+H]$^+$)

4-Arylisoxazole-cyclohexanecarboxylic acid ester intermediates of formula (IX-1)

General Procedure (III): Arylisoxazole Formation

To a solution of an oxime intermediate of formula VII (1 eq) in tetrahydrofuran (0.1-0.2 M) is added potassium tort-butoxide (1.3 eq) at 0° C. The cooling bath is removed 15 minutes after completed addition, and the reaction mixture is stirred for 2-24 h at room temperature. The reaction mixture is partitioned between an organic solvent such as ethyl acetate or tort-butyl methyl ether and water. The layers are separated. The aqueous layer is extracted with one or two portions of organic solvent. The combined organic layers are dried over anhydrous sodium sulfate and concentrated to dryness. Purification by flash-chromatography gives a 4-arylisoxazole-cyclohexanecarboxylic acid ester intermediate of formula (IX-1).

4-Arylisoxazole-cyclohexanecarboxylic acid ester 1 trans-4-(6-Fluoro-benzo[d]isoxazol-3-yl)-cyclohexanecarboxylic acid methyl ester

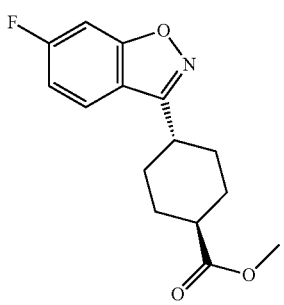 [SMILES: COC(=O)[C@H]1CC[C@H](c2noc3cc(F)ccc32)CC1]

The title compound was obtained as light brown solid in quantitative yield from trans-4-{(2,4-difluoro-phenyl)-[(E/Z)-hydroxyimino]-methyl}-cyclohexanecarboxylic acid methyl ester according to general procedure (III). MS m/e: 278 ([M+H]$^+$)

4-Arylisoxazole-cyclohexanecarboxylic acid ester 2 trans-4-(5-Fluoro-benzo[d]isoxazol-3-yl)-cyclohexanecarboxylic acid methyl ester

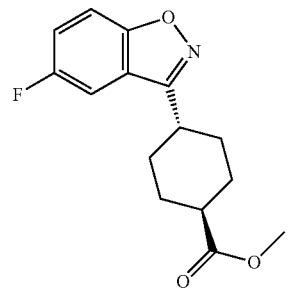 [SMILES: COC(=O)[C@H]1CC[C@H](c2noc3ccc(F)cc32)CC1]

The title compound was obtained as white solid in 52% yield from trans-4-{(2,5-difluoro-phenyl)-[(E/Z)-hydroxyimino]-methyl}-cyclohexanecarboxylic acid methyl ester according to general procedure (III) MS m/e: 278 ([M+H]$^+$)

4-Arylisoxazole-cyclohexanecarboxylic acid ester 3 trans-4-Isoxazolo[4,5-b]pyridin-3-yl-cyclohexanecarboxylic acid methyl ester

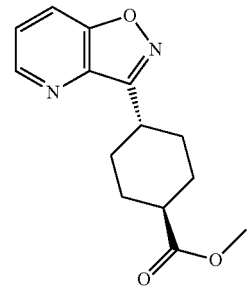

The title compound was obtained as off-white solid in 71% yield from trans-4-{(3-fluoro-pyridin-2-yl)-[(E/Z)-hydroxyimino]-methyl}-cyclohexanecarboxylic acid methyl ester according to general procedure (III). MS m/e: 261 ([M+H]$^+$)

4-Arylisoxazole-cyclohexanecarboxylic acid ester 4 trans-4-Isoxazolo[5,4-b]pyridin-3-yl-cyclohexanecarboxylic acid methyl ester

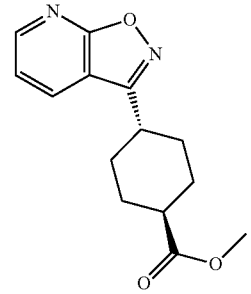 [SMILES: COC(=O)[C@H]1CC[C@H](c2noc3ncccc32)CC1]

The title compound was obtained as white solid in 46% yield from trans-4-{(2-chloro-pyridin-3-yl)-[(E/Z)-hydroxyimino]-methyl}-cyclohexanecarboxylic acid methyl ester according to general procedure (III). MS m/e: 261 ([M+H]⁺)

4-Arylisoxazole-cyclohexanecarboxylic acid intermediate of formula (X-1)

cis/trans-4-Benzo[d]isoxazol-3-yl-cyclohexanecarboxylic acid

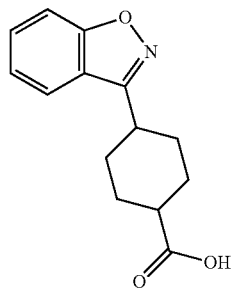 [SMILES: O=C(O)C1CCC(c2noc3ccccc23)CC1]

To a solution of cis/trans-4-{(2-fluoro-phenyl)-[(E/Z)-hydroxyimino]-methyl}-cyclohexanecarboxylic acid methyl ester (0.52 g, 1.9 mmol) in dry tetrahydrofuran (19 ml) was added sodium methoxide (0.13 g, 2.4 mmol) at room temperature. Stirring for 16 h was followed by addition of further sodium methoxide (0.13 g, 2.4 mmol) and stirring for 1 h at 60° C. After cooling to room temperature the reaction mixture was partitioned between tert-butyl methyl ether (100 ml) and 1M aqueous hydrogen chloride solution. The layers were separated. The aqueous layer was extracted with one 100-ml portion of tert-butyl methyl ether. The combined organic layers were dried over anhydrous sodium sulfate and concentrated to dryness. The residue was dissolved in a mixture of 1,4-dioxane (10 ml) and 2M aqueous sodium hydroxide solution (9.3 ml, 18.6 mmol) and stirred for 16 h. The mixture was partitioned between tert-butyl methyl ether (100 ml) and 1M aqueous sodium hydroxide solution (50 ml). The layers were separated. The organic layer was extracted with two 50-ml portions of 1M aqueous sodium hydroxide solution. The combined basic aqueous layers were poured on ice (100 g), acidified to pH 1 with concentrated hydrochloric acid and extracted with three 100-ml portions of ethyl acetate. The combined ethyl acetate layers were dried over anhydrous sodium sulfate and concentrated to dryness. Purification by flash-chromatography with n-heptane/ethyl acetate as eluent gave the title compound (0.36 g, 79%) as off-white solid. MS m/e: 244 ([M−H]⁻)

Thioether Intermediates of Formula (VIII)
General Procedure (IV): Thioether Formation A mixture of potassium tert-butoxide (1 eq) and benzyl mercaptane (1.1 eq) in dry tetrahydrofuran (0.3 M) is stirred for 5 min at room temperature under an inert gas atmosphere. A solution of 4-aroyl-cyclohexanecarboxylic acid ester intermediates of formula (VI) (1 eq) in tetrahydrofuran (0.3 M) is added and the reaction mixture is stirred for 16-24 h. The reaction mixture is partitioned between an organic solvent such as ethyl acetate or tert-butyl methyl ether and water. The layers are separated. The aqueous layer is extracted with one or two portions of organic solvent. The combined organic layers are dried over anhydrous sodium sulfate and concentrated to dryness. Purification by flash-chromatography gives a thioether intermediate of formula (VIII).

Thioether 1 trans-4-(2-Benzylsulfanyl-benzoyl)-cyclohexanecarboxylic acid methyl ester

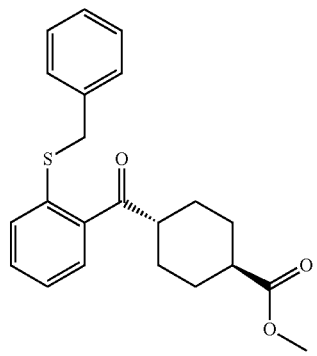 [SMILES: COC(=O)[C@H]1CC[C@H](C(=O)c2ccccc2SCc2ccccc2)CC1]

The title compound was obtained as yellow oil in 92% yield from trans-4-(2-fluoro-benzoyl)-cyclohexanecarboxylic acid methyl ester according to general procedure (IV). MS m/e: 369 ([M+H]⁺)

Thioether 2 trans-4-(3-Benzylsulfanyl-pyridine-2-carbonyl)-cyclohexanecarboxylic acid methyl ester

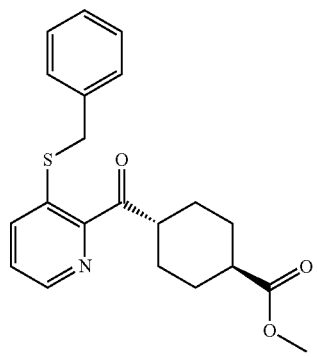 [SMILES: COC(=O)[C@H]1CC[C@H](C(=O)c2ncccc2SCc2ccccc2)CC1]

The title compound was obtained as yellow solid in 87% yield from trans-4-(3-fluoro-pyridine-2-carbonyl)-cyclohexanecarboxylic acid methyl ester according to general procedure (IV). MS m/e: 370 ([M+H]⁺)

Thioether 3 trans-4-(3-Benzylsulfanyl-pyridine-4-carbonyl)-cyclohexanecarboxylic acid methyl ester

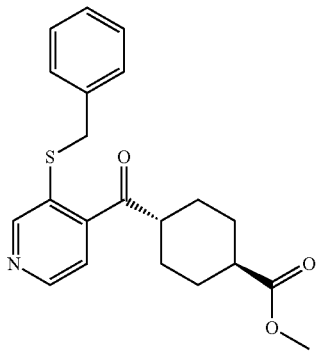 [SMILES: COC(=O)[C@H]1CC[C@H](C(=O)c2ccncc2SCc2ccccc2)CC1]

The title compound was obtained as yellow oil in 90% yield from trans-4-(3-fluoro-pyridine-4-carbonyl)-cyclohexanecarboxylic acid methyl ester according to general procedure (IV). MS m/e: 370 ([M+H]$^+$)

4-Arylisothiazole-cyclohexanecarboxylic acid ester intermediates of formula (IX-2)

General Procedure (V): Arylisothiazole Formation

To a solution of a thioether intermediate of formula (VIII) (1 eq) in dichloromethane (0.1 M) is added sulfuryl chloride (1.05 eq) at 0° C. The reaction mixture is stirred for 1 h. After evaporation of the solvent the residue is re-dissolved in tetrahydrofuran (0.1 M) followed by addition of 2M ethanolic ammonia solution (10 eq) at room temperature and stirring for 2-3 h. The reaction mixture is partitioned between an organic solvent such as ethyl acetate or tert-butyl methyl ether and saturated sodium bicarbonate solution. The layers are separated. The aqueous layer is extracted with one or two portions of organic solvent. The combined organic layers are dried over anhydrous sodium sulfate and concentrated to dryness. Purification by flash-chromatography gives 4-arylisothiazole-cyclohexanecarboxylic acid ester intermediate of formula (IX-2).

4-Arylisothiazole-cyclohexanecarboxylic acid ester 1 trans-4-Benzo[d]isothiazol-3-yl-cyclohexanecarboxylic acid methyl ester

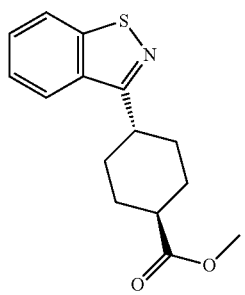 [SMILES: COC(=O)[C@H]1CC[C@H](c2nsc3ccccc32)CC1]

The title compound was obtained as white solid in 72% yield from trans-4-(2-benzylsulfanyl-benzoyl)-cyclohexanecarboxylic acid methyl ester according to general procedure (V). MS m/e: 276 ([M+H]$^+$)

4-Arylisothiazole-cyclohexanecarboxylic acid ester 2 trans-4-Isothiazolo[4,5-b]pyridin-3-yl-cyclohexanecarboxylic acid methyl ester

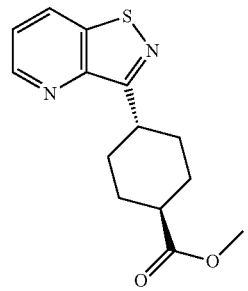 [SMILES: COC(=O)[C@H]1CC[C@H](c2nsc3cccnc32)CC1]

The title compound was obtained as light yellow oil in 90% yield from trans-4-(3-benzyl sulfanyl-pyridine-2-carbonyl)-cyclohexanecarboxylic acid methyl ester according to general procedure (V). MS m/e: 277 ([M+H]$^+$)

4-Arylisothiazole-cyclohexanecarboxylic acid ester 3 trans-4-Isothiazolo[5,4-c]pyridin-3-yl-cyclohexanecarboxylic acid methyl ester

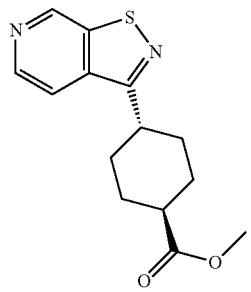 [SMILES: COC(=O)[C@H]1CC[C@H](c2nsc3cnccc32)CC1]

The title compound was obtained as colorless oil in 51% yield from trans-4-(3-benzylsulfanyl-pyridine-4-carbonyl)-cyclohexanecarboxylic acid methyl ester according to general procedure (V). MS m/e: 277 ([M+H]$^+$)

Hydrazide Intermediates of Formula (II)

General Procedure (VI): Hydrazide Formation from Acid

To a solution of a 4-heteroaryl-cyclohexanecarboxylic acid intermediate of formula (X) (1 eq) and triethylamine (1.05 eq) in tetrahydrofuran (0.2 M) is added ethyl chloroformate (1.05 eq) at 0° C. The reaction mixture is stirred at 0° C. for 1 h. The ammonium salts are removed by filtration. The filtrate is added to a cold solution of hydrazine hydrate (2 eq) in methanol (0.2 M). The reaction mixture is stirred at room temperature for 2-16 h. The solvent is evaporated under reduced pressure, and the residue is partitioned between an organic solvent such as ethyl acetate or dichloromethane and water. The organic layer is separated. The aqueous layer is extracted with two or three portions of organic solvent. The combined organic layers are dried over anhydrous sodium sulfate and concentrated in vacuo to give a hydrazide intermediate of formula (II), which is usually used in the next step without further purification.

General Procedure (VII): Hydrazide Formation from Ester

A mixture of a 4-heteroaryl-cyclohexanecarboxylic acid ester intermediate of formula (IX) (1 eq) and hydrazine hydrate (2-6 eq) in n-butanol (0.2-1 M) is heated at reflux for 16-72 h. After cooling to room temperature the reaction mixture is partitioned between an organic solvent such as ethyl acetate or dichloromethane and water. The layers are separated and the aqueous layer is extracted with two portions of organic solvent. The combined organic layers are dried over anhydrous sodium sulfate and concentrated in vacuo to give a hydrazide intermediate of formula (II), which is usually used in the next step without further purification.

Hydrazide 1 cis/trans-4-Benzo[d]isoxazol-3-yl-cyclohexanecarboxylic acid hydrazide

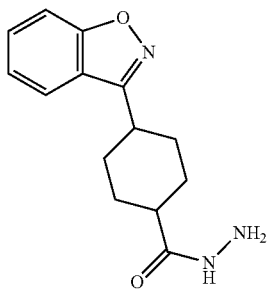 [SMILES: NNC(=O)C1CCC(c2noc3ccccc23)CC1]

The title compound was obtained as white solid in quantitative yield from cis/trans-4-benzo[d]isoxazol-3-yl-cyclohexanecarboxylic acid according to general procedure (VI). MS m/e: 260 ([M+H]$^+$)

Hydrazide 2 trans-4-(6-Fluoro-benzo[d]isoxazol-3-yl)-cyclohexanecarboxylic acid hydrazide

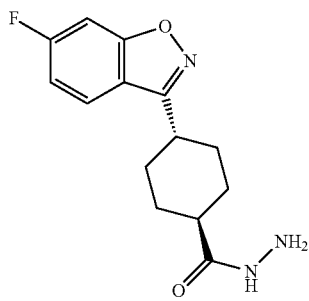 [SMILES: NNC(=O)[C@H]1CC[C@H](c2noc3cc(F)ccc32)CC1]

The title compound was obtained as white solid in 39% yield after flash-chromatography with n-heptane/isopropanol as eluent from trans-4-(6-fluoro-benzo[d]isoxazol-3-yl)-cyclohexanecarboxylic acid methyl ester according to general procedure (VII). MS m/e: 278 ([M+H]$^+$)

Hydrazide 3 trans-4-(5-Fluoro-benzo[d]isoxazol-3-yl)-cyclohexanecarboxylic acid hydrazide

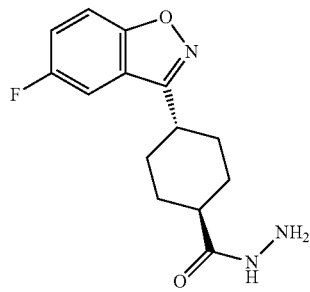 [SMILES: NNC(=O)[C@H]1CC[C@H](c2noc3ccc(F)cc32)CC1]

The title compound was obtained as white solid in quantitative yield from trans-4-(5-fluoro-benzo[d]isoxazol-3-yl)-cyclohexanecarboxylic acid methyl ester according to general procedure (VII). MS m/e: 278 ([M+H]$^+$)

Hydrazide 4 trans-4-Isoxazolo[4,5-b]pyridin-3-yl-cyclohexanecarboxylic acid hydrazide

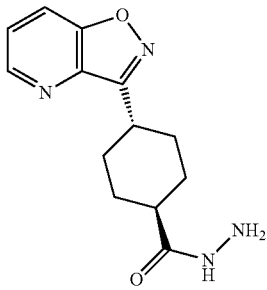 [SMILES: NNC(=O)[C@H]1CC[C@H](c2noc3cccnc32)CC1]

The title compound was obtained as white solid in quantitative yield from trans-4-isoxazolo[4,5-b]pyridin-3-yl-cyclohexanecarboxylic acid methyl ester according to general procedure (VII). MS m/e: 261 ([M+H]$^+$)

Hydrazide 5 trans-4-Isoxazolo[5,4-b]pyridin-3-yl-cyclohexanecarboxylic acid hydrazide

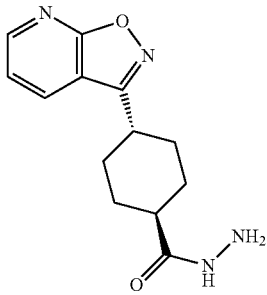 [SMILES: NNC(=O)[C@H]1CC[C@H](c2noc3ncccc32)CC1]

The title compound was obtained as white solid in quantitative yield from trans-4-isoxazolo[5,4-b]pyridin-3-yl-cyclohexanecarboxylic acid methyl ester according to general procedure (VII). MS m/e: 261 ([M+H]⁺)

Hydrazide 6 trans-4-Benzo[d]isothiazol-3-yl-cyclohexanecarboxylic acid hydrazide

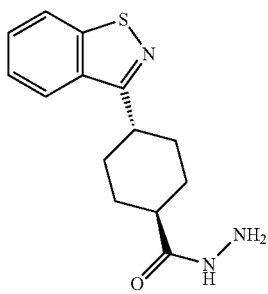 [SMILES: NNC(=O)[C@H]1CC[C@H](c2nsc3ccccc32)CC1]

The title compound was obtained as white solid in 62% yield from trans-4-benzo[d]isothiazol-3-yl-cyclohexanecarboxylic acid methyl ester according to general procedure (VII). MS m/e: 275 (M⁺)

Hydrazide 7 trans-4-Isothiazolo[4,5-h]pyridin-3-yl-cyclohexanecarboxylic acid hydrazide

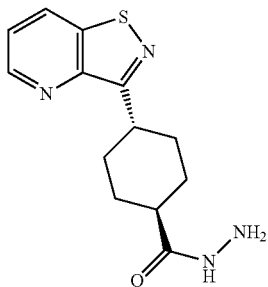 [SMILES: NNC(=O)[C@H]1CC[C@H](c2nsc3cccnc32)CC1]

The title compound was obtained as white solid in 67% yield from trans-4-isothiazolo[4,5-h]pyridin-3-yl-cyclohexanecarboxylic acid methyl ester according to general procedure (VII) MS m/e: 277 ([M+H]⁺)

Hydrazide 8 trans-4-Isothiazolo[5,4-c]pyridin-3-yl-cyclohexanecarboxylic acid hydrazide

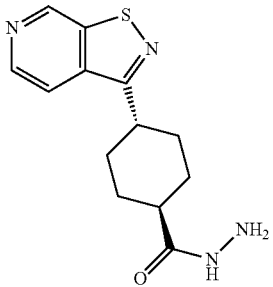 [SMILES: NNC(=O)[C@H]1CC[C@H](c2nsc3cnccc32)CC1]

The title compound was obtained as white solid in 63% yield from trans-4-isothiazolo[5,4-c]pyridin-3-yl-cyclohexanecarboxylic acid methyl ester according to general procedure (VII). MS m/e: 277 ([M+H]⁺)

Hydrazide 9 cis-4-Benzo[d]isothiazol-3-yl-cyclohexanecarboxylic acid hydrazide

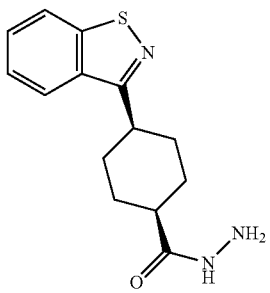 [SMILES: NNC(=O)[C@H]1CC[C@@H](c2nsc3ccccc32)CC1]

The title compound was obtained as white solid according to general procedure (VI) from a cis/trans-mixture of 4-benzo[d]isothiazol-3-yl-cyclohexanecarboxylic acid in 10% yield after removal of a portion of the trans-isomer, which had precipitated upon trituration from tert-butyl methyl ether, by filtration and chromatographic separation. MS m/e: 276 ([M+H]⁺)

Thiolactam Intermediates of Formula III

7-Chloro-2-thioxo-1,2,3,5-tetrahydro-benzo[e][1,4]diazepine-4-carboxylic acid tert-butyl ester a) 4-Chloro-2-chloromethyl-1-nitro-benzene To a solution of 5-chloro-2-nitrobenzyl alcohol (80 g, 0.42 mol) and triethylamine (64 ml, 0.46 mol) in dichloromethane (840 ml) was added drop wise thionyl chloride (34 ml, 0.46 mol) during a period of 30 minutes while the internal temperature was kept below 32° C. by cooling with a water bath. The reaction mixture was stirred for 3 h. The solvent was evaporated and the residue was triturated in warm tert-butyl methyl ether (970 ml). The ammonium salts were removed by filtration and the filtrate was concentrated in vacuo to give the title compound (85 g, 99%) as brown oil which was used in the next step without purification. MS m/e: 205 (M⁺).

b) (5-Chloro-2-nitro-benzylamino)-acetic acid ethyl ester

A mixture of 4-chloro-2-chloromethyl-1-nitro-benzene (85 g, 0.41 mol), glycine ethyl ester hydrochloride (70 g, 0.50 mol) and triethylamine (121.4 ml, 0.8665 mol) in ethanol (1000 ml) was heated at reflux for 8 h. The solvent was evaporated and the residue was triturated in warm tert-butyl methyl ether. The ammonium salts were removed by filtration and the filtrate was concentrated in vacuo to give the title compound (111 g, 99%) as an amorphous brown solid which was used in the next step without purification. MS m/e: 273 (M+H⁺).

c) [tert-Butoxycarbonyl-(5-chloro-2-nitro-benzyl)-amino]-acetic acid ethyl ester A solution of (5-chloro-2-nitro-benzylamino)-acetic acid ethyl ester (110 g, 0.403 mol), di-tort-butyl dicarbonate (180 g, 0.807 mol) and 4-N,N-dimethylaminopyridine (2.51 g, 0.0202 mol) in dichloromethane (1200 ml) was stirred for 2 h at 0° C. and further 16 h at room temperature. The solvent was evaporated and the crude product was purified by flash chromatography with a cyclohexane/ethyl acetate mixture as eluent to give the title compound (76.4 g, 51%) as light yellow viscous oil. MS m/e: 373 (M+H$^+$).

d) [(2-Amino-5-chloro-benzyl)-tert-butoxycarbonyl-amino]-acetic acid ethyl ester To a solution of [tert-butoxycarbonyl-(5-chloro-2-nitro-benzyl)-amino]-acetic acid ethyl ester (69.0 g, 0.186 mol) in ethyl acetate (1200 ml) was added zinc bromide (8.5 g, 0.037 mol). The reaction mixture was purged with argon after 15 minutes. After addition of the palladium catalyst (10% on activated charcoal, 7.9 g, 0.0074 mol) the mixture was hydrogenated at ambient pressure during a period of ca. 48 h until ca. 13 l of hydrogen gas had been consumed. The catalyst was removed by filtration and the filtrate was washed with two portions of saturated aqueous sodium bicarbonate solution and brine, each. The organic layer was dried over anhydrous sodium sulfate and concentrated in vacuo to give the title compound (60.6 g, 95.5%) as yellow waxy solid. MS m/e: 343 (M+H$^+$).

e) 7-Chloro-2-oxo-1,2,3,5-tetrahydro-benzo[1,4]diazepine-4-carboxylic acid tert-butyl ester To a solution of [(2-amino-5-chloro-benzyl)-tert-butoxycarbonyl-amino]acetic acid ethyl ester (60 g, 0.18 mol) in tetrahydrofuran (600 ml) was added potassium tert-butoxide (22 g, 0.19 mol) in small portions at 5° C. under cooling on an ice-water batch. After completed addition the cooling bath was removed and reaction mixture was stirred for 3 h at room temperature followed by addition of water (400 ml), saturated aqueous ammonium chloride solution (280 ml) and ethyl acetate (800 ml). After 10 minutes the precipitate was collected by filtration. The layers were separated from the filtrate, dried over anhydrous sodium sulfate and concentrated in vacuo. The residue was combined with the precipitate, which had previously been collected by filtration, and crystallized from hot ethyl acetate to give the title compound (46 g, 88%) as white solid. MS m/e: 295 (M−H$^+$).

f) 7-Chloro-2-thioxo-1,2,3,5-tetrahydro-benzo[e][1,4]diazepine-4-carboxylic acid tert-butyl ester A mixture of 7-chloro-2-oxo-1,2,3,5-tetrahydro-benzo[1,4]diazepine-4-carboxylic acid tert-butyl ester (41.1 g, 0.139 mol) and 2,4-bis-(4-methoxyphenyl)-1,3,2,4-dithiadiphosphetane-2,4-disulfide (31.5 g, 0.0763 mol) in tetrahydrofuran (1100 ml) was heated at reflux for 3 h. The solvent was evaporated and the residue was triturated in tert-butyl methyl ether. The precipitate was removed by filtration and the filtrate was concentrated to dryness. The residue was crystallized from hot ethanol to give the title compound (37.5 g, 86.4%) as light yellow solid. MS m/e: 311 (M−H$^+$).

7-Fluoro-2-thioxo-1,2,3,5-tetrahydro-benzo[e][1,4]diazepine-4-carboxylic acid tert-butyl ester The title compound was obtained as light yellow solid in comparable yields according to the procedures described above for the synthesis of 7-chloro-2-thioxo-1,2,3,5-tetrahydro-benzo[e][1,4]diazepine-4-carboxylic acid tert-butyl ester using 5-fluoro-2-nitrobenzyl alcohol instead of 5-chloro-2-nitrobenzyl alcohol in step a). MS m/e: 297 (M−H$^+$).

General Procedure (VIII): Condensation of Hydrazide and Thiolactam to Triazole

A mixture of a hydrazide of formula II (1-1.5 eq) and a thiolactam of formula III (1 eq) in n-butanol (0.1-0.2 M) is heated at reflux for 16-72 h. After cooling to room temperature the solvent is evaporated and the residue is purified by flash-chromatography to give a compound of formula I. When a thiolactam of formula III-1 (compounds of formula III in Which R$^1$ is tert-butoxycarbonyl) is used the N-tert-butoxycarbonyl group of the resulting triazole product of formula I-1 can be partially or completely cleaved thermally, and a secondary amine of formula I-2 is obtained in addition or as the sole product.

General Procedure (IX-a): Cleavage of N-Tert-Butoxycarbonyl (N-BOC) Group

A solution of an N-BOC derivative of formula I-1 (1 eq) in 1.25 M methanolic or 1.5 M ethanolic hydrogen chloride solution (10-20 eq HCl) is heated at 50° C. for 15-60 minutes. After cooling to room temperature the reaction mixture is concentrated in vacuo to give a secondary amine of formula I-2 as hydrochloride salt. Optionally the free base can be obtained by partitioning the hydrochloride salt between 1 M aqueous sodium hydroxide solution and an organic solvent, e.g. ethyl acetate or dichloromethane. The layers are separated and the aqueous layer is extracted with two portions of the organic solvent. The combined organic layers are dried over anhydrous sodium sulfate, filtered and concentrated in vacuo to give the free base of a compound of formula I-2.

General Procedure (IX-b): Cleavage of N-Tert-Butoxycarbonyl (N-BOC) Group

A solution of an N-BOC derivative of general formula I-1 (1 eq) and trifluoroacetic acid (10-20 eq) in dichloromethane is stirred at room temperature for 6-24 h. The reaction mixture is partitioned between 1 M aqueous sodium hydroxide solution and an organic solvent such as ethyl acetate or dichloromethane. The layers are separated and the aqueous layer is extracted with two portions of the organic solvent. The combined organic layers are dried over anhydrous sodium sulfate, filtered and concentrated in vacuo to give the free base of a compound of formula I-2.

General Procedure (X): Reductive N-Alkylation

A mixture of a compound of formula I-2 as free base or as hydrochloride salt (1 eq, 0.1-0.2 M), triethylamine (1 eq when the hydrochloride salt of a compound of formula I-2 is used) and an aldehyde or ketone (8 eq) in methanol is heated at reflux for 2-6 h. After cooling to 0° C. sodium cyanoborohydride (2-3 eq) is added. The reaction mixture is stirred for 3-16 h at room temperature and quenched with 1 M aqueous sodium hydroxide solution. The aqueous layer is extracted with ethyl acetate. The combined organic layers are dried over anhydrous sodium sulfate and concentrated in vacuo. Flash chromatography gives an N-alkyl compound of formula I.

General Procedure (XI): Reductive N-Methylation

A mixture of a compound of formula I-2 as free base (1 eq, 0.1-0.2 M), sodium acetate (1.1 eq), acetic acid (1.1 eq) and an aqueous formaldehyde solution (36%, 1.4 eq) in dichloromethane is stirred for 0.5-2 h. After cooling to 0° C. sodium triacetoxyborohydride (1.6 eq) is added. The reaction mixture is stirred for 2-16 h at room temperature and quenched with 1 M aqueous sodium hydroxide solution. The aqueous layer is extracted with ethyl acetate. The combined organic layers are dried over anhydrous sodium sulfate and concentrated in vacuo. Flash chromatography gives an N-methyl compound of formula I-3.

Example 1 cis-1-(4-Benzo[d]isoxazol-3-yl-cyclohexyl)-8-chloro-4H,6H-2,3,5,10b-tetraaza-benzo[e]azulene-5-carboxylic acid tert-butyl ester (cis/trans=92:8) and

Example 2 trans-1-(4-Benzo[d]isoxazol-3-yl-cyclohexyl)-8-chloro-4H,6H-2,3,5,10b-tetraaza-benzo[e]azulene-5-carboxylic acid tert-butyl ester cis/trans-1-(4-Benzo[d]isoxazol-3-yl-cyclohexyl)-8-chloro-4H,6H-2,3,5,10b-tetraaza-benzo[e]azulene-5-carboxylic acid tert-butyl ester (92:8) and trans-1-(4-benzo[e]isoxazol-3-yl-cyclohexyl)-8-chloro-4H,6H-2,3,5,10b-tetraaza-benzo[e]azulene-5-carboxylic acid tert-butyl ester were obtained according to general procedure (VIII) after chromatographic separation.
Hydrazide: cis/trans-4-Benzo[d]isoxazol-3-yl-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester
cis-1-(4-Benzo[d]isoxazol-3-yl-cyclohexyl)-8-chloro-4H,6H-2,3,5,10b-tetraaza-benzo[e]azulene-5-carboxylic acid tort-butyl ester (92:8) was obtained as white solid in 35% yield. MS m/e: 520 ([M+H]$^+$)
trans-1-(4-benzo[d]isoxazol-3-yl-cyclohexyl)-8-chloro-4H,6H-2,3,5,10b-tetraaza-benzo[e]azulene-5-carboxylic acid tert-butyl ester was obtained as white solid in 35% yield. MS m/e: 520 ([M+H]$^+$)

Example 3 cis-1-(4-Benzo[d]isoxazol-3-yl-cyclohexyl)-8-chloro-5,6-dihydro-4H-2,3,5,10b-tetraaza-benzo[e]azulene hydrochloride (cis/trans=92:8)

The title compound was obtained as white solid in quantitative yield from cis-1-(4-benzo[c]isoxazol-3-yl-cyclohexyl)-8-chloro-4H,6H-2,3,5,10b-tetraaza-benzo[e]azulene-5-carboxylic acid tert-butyl ester (cis/trans=92:8) according to general procedure (IX-a). MS m/e: 420 ([M+H]$^+$)

Example 4 cis-1-(4-Benzo[d]isoxazol-3-yl-cyclohexyl)-8-chloro-5-methyl-5,6-dihydro-4H-2,3,5,10b-tetraaza-benzo[e]azulene The title compound was obtained as white solid in 55% yield from cis-1-(4-benzo[c]isoxazol-3-yl-cyclohexyl)-8-chloro-5,6-dihydro-4H-2,3,5,10b-tetraaza-benzo[e]azulene hydrochloride (cis/trans=92:8) and paraformaldehyde according to general procedure (X). MS m/e: 420 ([M+H]$^+$)

Example 5 trans-1-(4-Benzo[d]isoxazol-3-yl-cyclohexyl)-8-chloro-5,6-dihydro-4H-2,3,5,10b-tetraaza-benzo[e]azulene hydrochloride The title compound was obtained as white solid in quantitative yield from trans-1-(4-benzo[d]isoxazol-3-yl-cyclohexyl)-8-chloro-4H,6H-2,3,5,10b-tetraaza-benzo[e]azulene-5-carboxylic acid tert-butyl ester according to general procedure (IX-a). MS m/e: 420 ([M+H]$^+$)

Example 6 trans-1-(4-Benzo[d]isoxazol-3-yl-cyclohexyl)-8-chloro-5-methyl-5,6-dihydro-4H-2,3,5,10b-tetraaza-benzo[e]azulene The title compound was obtained as white solid in 55% yield from trans-1-(4-benzo[d]isoxazol-3-yl-cyclohexyl)-8-chloro-5,6-dihydro-4H-2,3,5,10b-tetraaza-benzo[e]azulene hydrochloride and paraformaldehyde according to general procedure (X). MS m/e: 434 ([M+H]$^+$)

Example 7 trans-8-Chloro-[4-(6-fluoro-benzo[d]isoxazol-3-yl)-cyclohexyl]-4H,6H-2,3,5,10b-tetraaza-benzo[e]azulene-5-carboxylic acid tert-butyl ester The title compound was obtained as off-white solid in 33% yield according to general procedure (VIII).
Hydrazide: trans-4-(6-Fluoro-benzo[d]isoxazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 538 ([M+H]$^+$)

Example 8 trans-8-Chloro-1-[4-(6-fluoro-benzo[d]isoxazol-3-yl)-cyclohexyl]-5,6-dihydro-4H-2,3,5,10b-tetraaza-benzo[e]azulene hydrochloride The title compound was obtained as off-white solid in quantitative yield from trans-8-chloro-1-[4-(6-fluoro-benzo[d]isoxazol-3-yl)-cyclohexyl]-4H,6H-2,3,5,10b-tetraaza-benzo[e]azulene-5-carboxylic acid tert-butyl ester according to general procedure (IX-a). MS m/e: 438 ([M+H]$^+$)

Example 9 trans-8-Chloro-1-[4-(6-fluoro-benzo[d] isoxazol-3-yl)-cyclohexyl]-5-methyl-5,6-dihydro-4H-2,3,5,10b-tetraaza-benzo[e]azulene The title compound was obtained as white solid in 62% yield from trans-8-chloro-1-[4-(6-fluoro-benzo[d]isoxazol-3-yl)-cyclohexyl]-5,6-dihydro-4H-2,3,5,10b-tetraaza-benzo[e]azulene hydrochloride and paraformaldehyde according to general procedure (X). MS m/e: 452 ([M+H]$^+$)

Example 10 trans-8-Chloro-1-[4-(5-fluoro-benzo[d]isoxazol-3-yl)-cyclohexyl]-4H,6H-2,3,5,10b-tetraaza-benzo[e]azulene-5-carboxylic acid tert-butyl ester The title compound was obtained as white solid in 34% yield according to general procedure (VIII).
Hydrazide: trans-4-(5-Fluoro-benzo[d]isoxazol-3-yl)-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 538 ([M+H]$^+$)

Example 11 trans-8-Chloro-1-[4-(5-fluoro-benzo[d]isoxazol-3-yl)-cyclohexyl]-5,6-dihydro-4H-2,3,5,10b-tetraaza-benzo[e]azulene hydrochloride The title compound was obtained as white solid in 92% yield from trans-8-chloro-1-[4-(5-fluoro-benzo[d]isoxazol-3-yl)-cyclohexyl]-4H,6H-2,3,5,10b-tetraaza-benzo[e]azulene-5-carboxylic acid tert-butyl ester according to general procedure (IX-a). MS m/e: 438 ([M+H]$^+$)

Example 12 trans-8-Chloro-1-[4-(5-fluoro-benzo[d]isoxazol-3-yl)-cyclohexyl]-5-methyl-5,6-dihydro-4H-2,3,5,10b-tetraaza-benzo[e]azulene The title compound was obtained as white solid in 75% yield from trans-8-chloro-1-[4-(5-fluoro-benzo[d]isoxazol-3-yl)-cyclohexyl]-5,6-dihydro-4H-2,3,5,10b-tetraaza-benzo[e]azulene hydrochloride and paraformaldehyde according to general procedure (X). MS m/e: 452 ([M+H]$^+$)

Example 13 trans-8-Chloro-1-(4-isoxazolo[4,5-b]pyridin-3-yl-cyclohexyl)-4H,6H-2,3,5,10b-tetraaza-benzo[e]azulene-5-carboxylic acid tert-butyl ester The title compound was obtained as off-white solid in 21% yield according to general procedure (VIII).
Hydrazide: trans-4-Isoxazolo[5,4-b]pyridin-3-yl-cyclohexanecarboxylic acid hydrazide
Thiolactam: 7-Chloro-2-thioxo-1,2,3,5-tetrahydro-benzo[e][1,4]diazepine-4-carboxyli c acid tert-butyl ester. MS m/e: 521 ([M+H]$^+$)

Example 14 trans-8-Chloro-1-(4-isoxazolo[4,5-b]pyridin-3-yl-cyclohexyl)-5,6-dihydro-4H-2,3,5,10b-tetraaza-benzo[e]azulene hydrochloride The title compound was obtained as white solid in 94% yield from trans-8-chloro-1-(4-isoxazol o[4,5-b]pyridin-3-yl-cyclohexyl)-4H,6H-2,3,5,10b-tetraaza-benzo[e]azulene-5-carboxylic acid tert-butyl ester according to general procedure (IX-a). MS m/e: 421 ([M+H]$^+$)

Example 15 trans-8-Chloro-1-(4-isoxazolo[4,5-b]pyridin-3-yl-cyclohexyl)-5-methyl-5,6-dihydro-4H-2,3,5,10b-tetraaza-benzo[e]azulene The title compound was obtained as white solid in 75% yield from trans-8-chloro-1-(4-isoxazol o[4,5-b]pyridin-3-yl-cyclohexyl)-5,6-dihydro-4H-2,3,5,10b-tetraaza-benzo[e]azulene hydrochloride and paraformaldehyde according to general procedure (X). MS m/e: 435 ([M+H]$^+$)

Example 16 trans-8-Chloro-1-(4-isoxazolo[5,4-b]pyridin-3-yl-cyclohexyl)-4H,6H-2,3,5,10b-tetraaza-benzo[e]azulene-5-carboxylic acid tert-butyl ester The title compound was obtained as light yellow solid in 50% yield according to general procedure (VIII).
Hydrazide: trans-4-Isoxazolo[4,5-b]pyridin-3-yl-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 521 ([M+H]$^+$)

Example 17 trans-8-Chloro-1-(4-isoxazolo[5,4-b]pyridin-3-yl-cyclohexyl)-5,6-dihydro-4H-2,3,5,10b-tetraaza-benzo[e]azulene hydrochloride The title compound was obtained as light yellow solid in quantitative yield from trans-8-chloro-1-(4-isoxazolo[5,4-b]pyridin-3-yl-cyclohexyl)-4H,6H-2,3,5,10b-tetraaza-benzo[e]azulene-5-carboxylic acid tert-butyl ester according to general procedure (IX-a). MS m/e: 421 ([M+H]$^+$)

Example 18 trans-8-Chloro-1-(4-isoxazolo[5,4-b]pyridin-3-yl-cyclohexyl)-5-methyl-5,6-dihydro-4H-2,3,5,10b-tetraaza-benzo[e]azulene The title compound was obtained as white solid in 76% yield from trans-8-chloro-1-(4-isoxazolo[5,4-b]pyridin-3-yl-cyclohexyl)-5,6-dihydro-4H-2,3,5,10b-tetraaza-benzo[e]azulene hydrochloride and paraformaldehyde according to general procedure (X). MS m/e: 435 ([M+H]$^+$)

Example 19 trans-1-(4-Benzo[d]isothiazol-3-yl-cyclohexyl)-8-chloro-4H,6H-2,3,5,10b-tetraaza-benzo[e]azulene-5-carboxylic acid tert-butyl ester The title compound was obtained as off-white solid in 63% yield according to general procedure (VIII).
Hydrazide: trans-4-Benzo[d]isothiazol-3-yl-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 536 ([M+H]$^+$)

Example 20 trans-1-(4-Benzo[d]isothiazol-3-yl-cyclohexyl)-8-chloro-5,6-dihydro-4H-2,3,5,10b-tetraaza-benzo[e]azulene hydrochloride The title compound was obtained as off-white solid in quantitative yield from trans-1-(4-benzo[d]isothiazol-3-yl-cyclohexyl)-8-chloro-4H,6H-2,3,5,10b-tetraaza-benzo[e]azulene-5-carboxylic acid tert-butyl ester according to general procedure (IX-a). MS m/e: 436 ([M+H]$^+$)

Example 21 trans-1-(4-Benzo[d]isothiazol-3-yl-cyclohexyl)-8-chloro-5-methyl-5,6-dihydro-4H-2,3,5,10b-tetraaza-benzo[e]azulene The title compound was obtained as white solid in 86% yield from trans-1-(4-benzo[d]isothiazol-3-yl-cyclohexyl)-8-chloro-5,6-dihydro-4H-2,3,5,10b-tetraaza-benzo[e]azulene hydrochloride and paraformaldehyde according to general procedure (X). MS m/e: 450 ([M+H]$^+$)

Example 22 trans-1-(4-Benzo[d]isothiazol-3-yl-cyclohexyl)-8-chloro-5-cyclobutyl-5,6-dihydro-4H-2,3,5,10b-tetraaza-benzo[e]azulene A solution of trans-1-(4-benzo[d]isothiazol-3-yl-cyclohexyl)-8-chloro-5,6-dihydro-4H-2,3,5,10b-tetraaza-benzo[e]azulene (35.0 mg, 0.0803 mmol), cyclobutanone (11.3 mg, 0.161 mmol) and acetic acid (0.009 ml, 0.2 mmol) in 1,2-dichloroethane (0.8 ml) was stirred at room temperature for 20 h. After addition of sodium triacetoxyborohydride (37.4 mg, 0.177 mmol) the mixture was stirred for 1 h. Addition of methanol (0.5 ml) and N-ethyl diisopropylamine (0.028 ml, 0.16 mmol) to the reaction mixture was followed by concentration in vacuo. Preparative RP-HPLC with water (0.05% formic acid)/methanol as eluent gave the title compound (27 mg, 69%) as white solid. MS m/e: 490 ([M+H]$^+$)

Example 23 trans-{2-[1-(4-Benzo[d]isothiazol-3-yl-cyclohexyl)-8-chloro-4H,6H-2,3,5,10b-tetraaza-benzo[e]azulen-5-yl]-ethyl}-methyl-amine A mixture of trans-1-(4-benzo[d]isothiazol-3-yl-cyclohexyl)-8-chloro-5,6-dihydro-4H-2,3,5,10b-tetraaza-benzo[e]azulene (35.0 mg, 0.0803 mmol), cesium carbonate (105 mg, 0.321 mmol) and 2-methylaminoethyl chloride hydrochloride (41.8 mg, 0.321 mmol) in acetonitrile (0.8 ml) was heated at 70° C. for 20 h. After cooling to room temperature the reaction mixture was partitioned between 1 M aqueous sodium hydroxide solution (2 ml) and ethyl acetate (5 ml). The layers were separated. The aqueous layer was extracted with three 5-ml portions of ethyl acetate. The combined organic layers were concentrated in vacuo. Preparative RP-HPLC with water (0.05% formic acid)/methanol as eluent gave title compound (19 mg, 48%) as off-white solid. MS m/e: 493 ([M+H]$^+$)

Example 24 trans-1-[1-(4-Benzo[d]isothiazol-3-yl-cyclohexyl)-8-chloro-4H,6H-2,3,5,10b-tetraaza-benzo[e]azulen-5-yl]-ethanone To a solution of trans-1-(4-benzo[d]isothiazol-3-yl-cyclohexyl)-8-chloro-5,6-dihydro-4H-2,3,5,10b-tetraaza-benzo[e]azulene (35 mg, 0.080 mmol) and triethylamine (0.022 ml, 0.16 mmol) in dichloromethane (0.8 ml) was added acetyl chloride (0.011 ml, 0.16 mmol) at room temperature. Stirring for 20 h was followed by partitioning between water (20 ml) and ethyl acetate (25 ml). The layers were separated. The organic layer was washed with two 25 ml-portions of water. The organic layer was concentrated in vacuo. Preparative RP-HPLC with water (0.05% formic acid)/methanol as eluent gave the title compound (26 mg, 68%) as white solid. MS m/e: 478 ([M+H]$^+$)

Example 25 trans-1-[1-(4-Benzo[d]isothiazol-3-yl-cyclohexyl)-8-chloro-4H,6H-2,3,5,10b-tetraaza-benzo[e]azulen-5-yl]-2-dimethylamino-ethanone A solution of N,N-dimethylglycine (9.9 mg, 0.096 mmol) and HATU (37 mg, 0.096 mmol) in N,N-dimethylformamide (0.8 ml) was stirred for 5 minutes at room temperature. trans-1-(4-Benzo[d]isothiazol-3-yl-cyclohexyl)-8-chloro-5,6-dihydro-4H-2,3,5,10b-tetraaza-benzo[e]azulene (35 mg, 0.080 mmol) and N-ethyldiisopropylamine (0.033 ml, 0.19 mmol) were consecutively added. The reaction mixture was stirred for 20 h. Preparative RP-HPLC with water (0.05% formic acid)/methanol as eluent gave the formate salt of the title compound, which was liberated to the free base by filtration over aminopropyl modified silicagel with methanol (20 ml) as eluent. The filtrate was concentrated to dryness. The residue was redissolved in ethyl acetate, filtered and concentrated to dryness to give the title compound (21 mg, 50%) as off-white solid. MS m/e: 521 ([M+H]$^+$)

Example 26 trans-1-(4-Benzo[d]isothiazol-3-yl-cyclohexyl)-8-chloro-5-methanesulfonyl-5,6-dihydro-4H-2,3,5,10b-tetraaza-benzo[e]azulene To a solution of trans-1-(4-benzo[d]isothiazol-3-yl-cyclohexyl)-8-chloro-5,6-dihydro-4H-2,3,5,10b-tetraaza-benzo[e]azulene (35 mg, 0.080 mmol) and triethylamine (0.022 ml, 0.16 mmol) in dichloromethane (0.8 ml) was added methanesulfonyl chloride (0.013 ml, 0.16 mmol) at room temperature. Stirring for 20 h was followed by quenching with methanol (0.5 ml). The mixture was concentrated in vacuo. Preparative RP-HPLC with water (0.05% formic acid)/methanol as eluent gave the title compound (34 mg, 82%) as white solid: MS m/e: 514 ([M+H]$^+$)

Example 27 trans-8-Chloro-1-(4-isothiazolo[4,5-b]pyridin-3-yl-cyclohexyl)-4H,6H-2,3,5,10b-tetraaza-benzo[e]azulene-5-carboxylic acid tert-butyl ester The title compound was obtained as white solid in 77% yield according to general procedure (VIII).
Hydrazide: trans-4-Isothiazolo[4,5-b]pyridin-3-yl-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 537 ([M+H]$^+$)

Example 28 trans-8-Chloro-1-(4-isothiazolo[4,5-b]pyridin-3-yl-cyclohexyl)-5,6-dihydro-4H-2,3,5,10b-tetraaza-benzo[e]azulene The title compound was obtained as off-white solid in 98% yield from trans-8-chloro-1-(4-isothiazolo[4,5-b]pyridin-3-yl-cyclohexyl)-4H,6H-2,3,5,10b-tetraaza-benzo[e]azulene-5-carboxylic acid tert-butyl ester according to general procedure (IX-a). MS m/e: 437 ([M+H]$^+$)

Example 29 trans-8-Chloro-1-(4-isothiazolo[4,5-b]pyridin-3-yl-cyclohexyl)-5-methyl-5,6-dihydro-4H-2,3,5,10b-tetraaza-benzo[e]azulene The title compound was obtained as white solid in 66% yield from trans-8-chloro-1-(4-isothiazolo[4,5-b]pyridin-3-yl-cyclohexyl)-5,6-dihydro-4H-2,3,5,10b-tetraaza-benzo[e]

Example 30 trans-8-Chloro-1-(4-isothiazolo[5,4-c]pyridin-3-yl-cyclohexyl)-4H,6H-2,3,5,10b-tetraaza-benzo[e]azulene-5-carboxylic acid tert-butyl ester The title compound was obtained as white foam in 73% yield according to general procedure (VIII).
Hydrazide: trans-4-Isothiazolo[5,4-c]pyridin-3-yl-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 537 ([M+H]$^+$)

Example 31 trans-8-Chloro-1-(4-isothiazolo[5,4-c]pyridin-3-yl-cyclohexyl)-5,6-dihydro-4H-2,3,5,10b-tetraaza-benzo[e]azulene The title compound was obtained as light yellow solid in quantitative yield from trans-8-chloro-1-(4-isothiazolo[5,4-c]pyridin-3-yl-cyclohexyl)-4H,6H-2,3,5,10b-tetraaza-benzo[e]azulene-5-carboxylic acid tert-butyl ester according to general procedure (IX-a). MS m/e: 437 ([M+H]$^+$)

Example 32 trans-8-Chloro-1-(4-isothiazolo[4,5-b]pyridin-3-yl-cyclohexyl)-5-methyl-5,6-dihydro-4H-2,3,5,10b-tetraaza-benzo[e]azulene The title compound was obtained as white solid in 33% yield from trans-8-chloro-1-(4-isothiazolo[5,4-c]pyridin-3-yl-cyclohexyl)-5,6-dihydro-4H-2,3,5,10b-tetraaza-benzo[e]azulene and paraformaldehyde according to general procedure (X). MS m/e: 451 ([M+H]$^+$).

Example 33 cis-1-(4-Benzo[d]isothiazol-3-yl-cyclohexyl)-8-chloro-4H,6H-2,3,5,10b-tetraaza-benzo[e]azulene-5-carboxylic acid tert-butyl ester The title compound was obtained as white solid in 75% yield according to general procedure (VIII).
Hydrazide: cis-4-Benzo[d]isothiazol-3-yl-cyclohexanecarboxylic acid hydrazide
Thiolactam: 7-Chloro-2-thioxo-1,2,3,5-tetrahydro-benzo[e][1,4]diazepine-4-carboxylic acid tert-butyl ester. MS m/e: 536 ([M+H]$^+$)

Example 34 cis-1-(4-Benzo[d]isothiazol-3-yl-cyclohexyl)-8-chloro-5,6-dihydro-4H-2,3,5,10b-tetraaza-benzo[e]azulene The title compound was obtained as white solid in quantitative yield from cis-1-(4-benzo[d]isothiazol-3-yl-cyclohexyl)-8-chloro-4H,6H-2,3,5,10b-tetraaza-benzo[e]azulene-5-carboxylic acid tert-butyl ester according to general procedure (IX-a). MS m/e: 436 ([M+H]$^+$)

Example 35 cis-1-(4-Benzo[d]isothiazol-3-yl-cyclohexyl)-8-chloro-5-methyl-5,6-dihydro-4H-2,3,5,10b-tetraaza-benzo[e]azulene The title compound was obtained as white solid in 52% yield from cis-1-(4-benzo[d]isothiazol-3-yl-cyclohexyl)-8-chloro-5,6-dihydro-4H-2,3,5,10b-tetraaza-benzo[e]azulene according to general procedure (XI). MS m/e: 450 ([M+H]$^+$)

The invention claimed is:
1. A compound of formula I

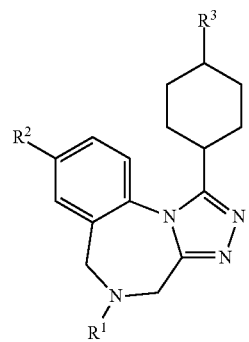

wherein
$R^1$ is selected from the group consisting of
i) H,
ii) —$C_{1-6}$-alkyl, unsubstituted or substituted by 1 to 5 substituents individually selected from the group consisting of OH, halogen, cyano and $C_{1-6}$-alkoxy,
iii) —$S(O)_2$—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
iv) —$C(O)$—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
v) —$C(O)O$—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy;
vi) cycloalkyl, unsubstituted or substituted by 1 to 5 substituents individually selected from the group consisting of OH, halogen, cyano, $C_{1-6}$-alkyl and $C_{1-6}$-alkoxy,
vii) —$S(O)_2$—$(CH_2)_q$—$NR^iR^{ii}$, wherein
q is 0 or 1,
$R^i$ and $R^{ii}$ is each individually selected from the group consisting of H and $C_{1-6}$-alkyl, or $R^i$ and $R^{ii}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy,
viii) —$(CH_2)_r$—$NR^{iii}R^{iv}$, wherein
R is 1, 2 or 3,
$R^{iii}$ and $R^{iv}$ is each individually selected from the group consisting of H and $C_{1-6}$-alkyl, or $R^{iii}$ and $R^{iv}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy, and ix) —C(O)(CH$_2$)$_s$—NR$^v$R$^{vi}$, wherein
s is 1, 2 or 3,
R$^v$ and R$^{vi}$ is each individually selected from the group consisting of H and $C_{1-6}$ alkyl, or R$^v$ and R$^{vi}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy;

R$^2$ is halogen;

R$^3$ is heterobiaryl, unsubstituted or substituted by 1-5 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy and hydroxy-$C_{1-6}$-alkyl;

or a pharmaceutically acceptable salt thereof.

2. The compound of claim 1, wherein R$^1$ is selected from the group consisting of
i) H,
ii) —$C_{1-6}$-alkyl,
iii) —S(O)$_2$—$C_{1-6}$-alkyl,
iv) —C(O)O—$C_{1-6}$-alkyl,
v) cycloalkyl,
vi) —(CH$_2$)$_r$—NR$^{iii}$R$^{iv}$, wherein
r is 1, 2 or 3,
R$^{iii}$ and R$^{iv}$ is each individually selected from the group consisting of H and $C_{1-6}$-alkyl, and
vii) —C(O)(CH$_2$)$_s$—NR$^v$R$^{vi}$, wherein
s is 1, 2 or 3,
R$^v$ and R$^{vi}$ is each individually selected from the group consisting of H and $C_{1-6}$-alkyl.

3. The compound of claim 1, wherein R$^1$ is selected from the group consisting of H, methyl, cyclobutyl, methyl-2-ethylamine, 1-oxo-ethyl, 1-oxo-2-(dimethylamino)-ethyl and methyl-sulfonyl.

4. The compound of claim 2, wherein R$^1$ is selected from the group consisting of —$C_{1-6}$-alkyl, cycloalkyl, —(CH$_2$)$_2$—N($C_{1-6}$-alkyl)$_2$ and —C(O)(CH$_2$)—N($C_{1-6}$-alkyl)$_2$.

5. The compound of claim 3, wherein R$^1$ is selected from the group consisting of methyl, cyclobutyl, methyl-2-ethylamine and 1-oxo-2-(dimethylamino)-ethyl.

6. The compound of claim 1, wherein R$^2$ is chloro.

7. The compound according to any of claim 1, wherein R$^3$ is heterobiaryl, unsubstituted or substituted by 1-2 halogen.

8. The compound of claim 7, wherein R$^3$ is benzo[d]isoxazolyl, isoxazolo[4,5-b]pyridinyl, isoxazolo[5,4-b]pyridinyl, benzo[d]isothiazolyl, isothiazolo[4,5-b]pyridinyl or 4-isothiazolo[5,4-c]pyridinyl, each unsubstituted or substituted by 1-2 halogen.

9. The compound of claim 7, wherein R$^3$ is benzo[d]isoxazol-3-yl, 6-fluoro-benzo[d]isoxazol-3-yl, 5-fluoro-benzo[d]isoxazol-3-yl, isoxazolo[4,5-b]pyridin-3-yl, isoxazolo[5,4-b]pyridin-3-yl, benzo[d]isothiazol-3-yl, isothiazolo[4,5-b]pyridin-3-yl or 4-isothiazolo[5,4-c]pyridin-3-yl.

10. A compound of claim 1, selected from the group consisting of cis-1-(4-Benzo[d]isoxazol-3-yl-cyclohexyl)-8-chloro-4H,6H-2,3,5,10b-tetraaza-benzo[e]azulene-5-carboxylic acid tert-butyl ester, trans-1-(4-Benzo[d]isoxazol-3-yl-cyclohexyl)-8-chloro-4H,6H-2,3,5,10b-tetraaza-benzo[e]azulene-5-carboxylic acid tert-butyl ester, cis-1-(4-Benzo[d]isoxazol-3-yl-cyclohexyl)-8-chloro-5,6-dihydro-4H-2,3,5,10b-tetraaza-benzo[e]azulene, cis-1-(4-Benzo[d]isoxazol-3-yl-cyclohexyl)-8-chloro-5-methyl-5,6-dihydro-4H-2,3,5,10b-tetraaza-benzo[e]azulene, trans-8-Chloro-1-[4-(6-fluoro-benzo[d]isoxazol-3-yl)-cyclohexyl]-4H,6H-2,3,5,10b-tetraaza-benzo[e]azulene-5-carboxylic acid tert-butyl ester, trans-8-Chloro-1-[4-(5-fluoro-benzo[d]isoxazol-3-yl)-cyclohexyl]-4H,6H-2,3,5,10b-tetraaza-benzo[e]azulene-5-carboxylic acid tert-butyl ester, trans-8-Chloro-1-[4-isoxazolo[4,5-b]pyridin-3-yl)-cyclohexyl]-4H,6H-2,3,5,10b-tetraaza-benzo[e]azulene-5-carboxylic acid tert-butyl ester, trans-8-Chloro-1-(4-isoxazolo[5,4-b]pyridin-3-yl-cyclohexyl)-4H,6H-2,3,5,10b-tetraaza-benzo[e]azulene-5-carboxylic acid tert-butyl ester, trans-1-(4-Benzo[d]isothiazol-3-yl-cyclohexyl)-8-chloro-4H,6H-2,3,5,10b-tetraaza-benzo[e]azulene-5-carboxylic acid tert-butyl ester, trans-8-Chloro-1-(4-isothiazolo[4,5-b]pyridin-3-yl-cyclohexyl)-4H,6H-2,3,5,10b-tetraaza-benzo[e]azulene-5-carboxylic acid tert-butyl ester, trans-8-Chloro-1-(4-isothiazolo[5,4-c]pyridin-3-yl-cyclohexyl)-4H,6H-2,3,5,10b-tetraaza-benzo[e]azulene-5-carboxylic acid tert-butyl ester, cis-1-(4-Benzo[d]isothiazol-3-yl-cyclohexyl)-8-chloro-4H,6H-2,3,5,10b-tetraaza-benzo[e]azulene-5-carboxylic acid tert-butyl ester, cis-1-(4-Benzo[d]isothiazol-3-yl-cyclohexyl)-8-chloro-5,6-dihydro-4H-2,3,5,10b-tetraaza-benzo[e]azulene, and cis-1-(4-Benzo[d]isothiazol-3-yl-cyclohexyl)-8-chloro-5-methyl-5,6-dihydro-4H-2,3,5,10b-tetraaza-benzo[e]azulene, or a pharmaceutically acceptable salt thereof.

11. A compound of claim 1, selected from the group consisting of trans-1-(4-Benzo[d]isoxazol-3-yl-cyclohexyl)-8-chloro-5,6-dihydro-4H-2,3,5,10b-tetraaza-benzo[e]azulene, trans-8-Chloro-1-[4-(6-fluoro-benzo[d]isoxazol-3-yl)-cyclohexyl]-5,6-dihydro-4H-2,3,5,10b-tetraaza-benzo[e]azulene, trans-8-Chloro-1-[4-(5-fluoro-benzo[d]isoxazol-3-yl)-cyclohexyl]-5,6-dihydro-4H-2,3,5,10b-tetraaza-benzo[e]azulene, trans-8-Chloro-1-(4-isoxazolo[4,5-b]pyridin-3-yl-cyclohexyl)-5,6-dihydro-4H-2,3,5,10b-tetraaza-benzo[e]azulene, trans-8-Chloro-1-(4-isoxazolo[5,4-b]pyridin-3-yl-cyclohexyl)-5,6-dihydro-4H-2,3,5,10b-tetraaza-benzo[e]azulene, trans-1-(4-Benzo[d]isothiazol-3-yl-cyclohexyl)-8-chloro-5,6-dihydro-4H-2,3,5,10b-tetraaza-benzo[e]azulene, trans-1-[1-(4-Benzo[d]isothiazol-3-yl-cyclohexyl)-8-chloro-4H,6H-2,3,5,10b-tetraaza-benzo[e]azulen-5-yl]-ethanone, trans-1-(4-Benzo[d]isothiazol-3-yl-cyclohexyl)-8-chloro-5-methanesulfonyl-5,6-dihydro-4H-2,3,5,10b-tetraaza-benzo[e]azulene, trans-8-Chloro-1-(4-isothiazolo[4,5-b]pyridin-3-yl-cyclohexyl)-5,6-dihydro-4H-2,3,5,10b-tetraaza-benzo[e]azulene, and trans-8-Chloro-1-(4-isothiazolo[5,4-c]pyridin-3-yl-cyclohexyl)-5,6-dihydro-4H-2,3,5,10b-tetraaza-benzo[e]azulene, or a pharmaceutically acceptable salt thereof.

12. A compound of claim 1, selected from the group consisting of trans-1-(4-Benzo[d]isoxazol-3-yl-cyclohexyl)-8-chloro-5-methyl-5,6-dihydro-4H-2,3,5,10b-tetraaza-benzo[e]azulene, trans-8-Chloro-1-[4-(6-fluoro-benzo[d]isoxazol-3-yl)-cyclohexyl]-5-methyl-5,6-dihydro-4H-2,3,5,10b-tetraaza-benzo[e]azulene, trans-8-Chloro-1-[4-(5-fluoro-benzo[d]isoxazol-3-yl)-cyclohexyl]-5-methyl-5,6-dihydro-4H-2,3,5,10b-tetraaza-benzo[e]azulene, trans-8-Chloro-1-(4-isoxazolo[4,5-b]pyridin-3-yl-cyclohexyl)-5-methyl-5,6-dihydro-4H-2,3,5,10b-tetraaza-benzo[e]azulene, trans-8-Chloro-1-(4-isoxazolo[5,4-b]pyridin-3-yl-cyclohexyl)-5-methyl-5,6-dihydro-4H-2,3,5,10b-tetraaza-benzo[e]azulene, trans-1-(4-Benzo[d]isothiazol-3-yl-cyclohexyl)-8-chloro-5-methyl-5,6-dihydro-4H-2,3,5,10b-tetraaza-benzo[e]azulene, trans-1-(4-Benzo[d]isothiazol-3-yl-cyclohexyl)-8-chloro-5-cyclobutyl-5,6-dihydro-4H-2,3,5,10b-tetraaza-benzo[e]azulene, trans-{2-[1-(4-Benzo[d]isothiazol-3-yl-cyclohexyl)-8-chloro-4H,6H-2,3,5,10b-tetraaza-benzo[e]azulen-5-yl]-ethyl}-methyl-amine, trans-1-[1-(4-Benzo[d]isothiazol-3-yl-cyclohexyl)-8-chloro-4H,6H-2,3,5,10b-tetraaza-benzo[e]azulen-5-yl]-2-dimethylamino-ethanone, trans-8-Chloro-1-(4-isothiazolo[4,5-b]pyridin-3-yl-cyclohexyl)-5-methyl-5,6-dihydro-4H-2,3,5,10b-tetraaza-benzo[e]azulene, and trans-8-Chloro-1-(4-isothiazolo[5,4-c]pyridin-3-yl-cyclohexyl)-5-methyl-5,6-dihydro-4H-2,3,5,10b-tetraaza-benzo[e]azulene, or a pharmaceutically acceptable salt thereof.

13. A pharmaceutical composition comprising a therapeutically effective amount of a compound of formula I

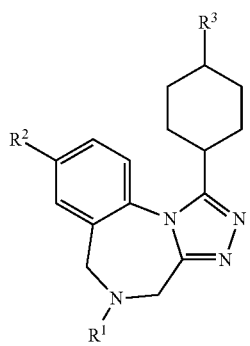

wherein
$R^1$ is selected from the group consisting of
i) H,
ii) —$C_{1-6}$-alkyl, unsubstituted or substituted by 1 to 5 substituents individually selected from the group consisting of OH, halogen, cyano and $C_{1-6}$-alkoxy,
iii) —$S(O)_2$—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
iv) —$C(O)$—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy,
v) —$C(O)O$—$C_{1-6}$-alkyl, wherein the $C_{1-6}$-alkyl is unsubstituted or substituted by 1 to 5 substituents individually selected from the group consisting of OH, halogen, cyano and $C_{1-6}$-alkoxy;
vi) cycloalkyl, unsubstituted or substituted by 1 to 5 substituents individually selected from the group consisting of OH, halogen, cyano, $C_{1-6}$-alkyl and $C_{1-6}$-alkoxy,
viii) —$S(O)_2$—$(CH_2)_q$—$NR^iR^{ii}$, wherein
q is 0 or 1,
$R^i$ and $R^{ii}$ is each individually selected from the group consisting of H and $C_{1-6}$-alkyl, or $R^i$ and $R^{ii}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy,
viii) —$(CH_2)_r$—$NR^{iii}R^{iv}$, wherein
r is 1, 2 or 3,
$R^{iii}$ and $R^{iv}$ is each individually, selected from the group consisting of H and $C_{1-6}$-alkyl, or $R^{iii}$ and $R^{iv}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy, and
ix) —$C(O)(CH_2)_s$—$NR^vR^{vi}$, wherein
s is 1, 2 or 3,
$R^v$ and $R^{vi}$ is each individually selected from the group consisting of H and $C_{1-6}$-alkyl, or $R^v$ and $R^{vi}$ form together with the nitrogen to which they are attached a 3- to 7-membered heterocyclyl comprising one or two heteroatoms individually selected from N, O and S, and which heterocyclyl is unsubstituted or substituted by 1 to 5 substituents individually selected from the group consisting of oxo, halogen, $C_{1-6}$-alkyl and $C_{1-6}$-alkoxy;
$R^2$ is halogen;
$R^3$ is heterobiaryl, unsubstituted or substituted by 1-5 substituents individually selected from the group consisting of OH, halogen, cyano, $C_{1-6}$-alkyl, $C_{1-6}$-alkoxy, halogen-$C_{1-6}$-alkyl, halogen-$C_{1-6}$-alkoxy and hydroxy-$C_{1-6}$-alkyl;
or a pharmaceutically acceptable salt thereof and a pharmaceutically acceptable carrier.

* * * * *